US006334778B1

(12) United States Patent
Brown

(10) Patent No.: US 6,334,778 B1
(45) Date of Patent: Jan. 1, 2002

(54) REMOTE PSYCHOLOGICAL DIAGNOSIS AND MONITORING SYSTEM

(75) Inventor: Stephen J. Brown, Woodside, CA (US)

(73) Assignee: Health Hero Network, Inc., Mountain View, CA (US)

( * ) Notice: Subject to any disclaimer, the term of this patent is extended or adjusted under 35 U.S.C. 154(b) by 0 days.

(21) Appl. No.: 09/271,188

(22) Filed: Mar. 17, 1999

Related U.S. Application Data

(63) Continuation-in-part of application No. 09/127,404, filed on Jul. 31, 1998, which is a continuation of application No. 08/843,495, filed on Apr. 16, 1997, now Pat. No. 5,828,943, which is a continuation of application No. 08/682,385, filed on Jul. 17, 1996, now abandoned, which is a continuation of application No. 08/479,570, filed on Jun. 7, 1995, now abandoned, which is a continuation of application No. 08/233,674, filed on Apr. 26, 1994, now abandoned, said application No. 09/127,404, is a continuation-in-part of application No.08/946,341, filed on Oct. 7, 1997.

(60) Provisional application No. 60/041,746, filed on Mar. 28, 1997, and provisional application No. 60/041,751, filed on Mar. 28, 1997.

(51) Int. Cl.[7] .................................................. G09B 7/00

(52) U.S. Cl. ........................ 434/258; 273/429; 273/430; 273/431; 273/432; 273/440; 434/236; 434/335; 434/362; 705/2

(58) Field of Search .................................. 434/258, 236, 434/335, 362; 273/429, 430, 431, 432, 440, 441, 445; 705/1, 2, 3

(56) References Cited

U.S. PATENT DOCUMENTS

| | | | | |
|---|---|---|---|---|
| 4,730,253 A | * | 3/1988 | Gordon | 434/335 |
| 4,978,303 A | * | 12/1990 | Lampbell | 434/258 |
| 5,230,629 A | * | 7/1993 | Buschke | 434/236 |
| 5,344,324 A | * | 9/1994 | O'Donnell | 434/258 |

OTHER PUBLICATIONS

Gardner et al.; "Comprehension and Appreciation of Humorous Material Following Brain Damage"; Brain; 98(3); pp. 399–412; DIALOG: File 155, Acc# 02064418, Sep. 1975.*

(List continued on next page.)

*Primary Examiner*—Stephen R. Tkacs
(74) *Attorney, Agent, or Firm*—Black Lowe & Graham PLLC

(57) ABSTRACT

A networked system for remotely assessing and monitoring psychological conditions. The system includes a server and a remote interface for entering in the server prompts, such as queries and instructions, to be responded to by the individual. The server is preferably a web server and the remote clinician interface is preferably a personal computer connected to the server via the Internet. The system also includes a remotely programmable patient apparatus connected to the server via a communication link, preferably the Internet. The patient apparatus interacts with the individual in accordance with a script received from the server. The server includes a script generator for generating the script from the set of prompts entered through the remote interface. The script is received and executed by the patient apparatus to communicate the prompts to the individual, to receive responses to the prompts, and to transmit the responses from the patient apparatus to the server. In accordance with the invention, the patient apparatus is programmed to prompt a patient to interactively operate one or more switches. Information recorded during an interactive diagnostic assessment procedure is analyzed to provide a health care professional with information that is helpful to determine whether clinical therapy and/or medication may be required. The preferred embodiment of the invention relates to diagnostic assessment of Attention Deficit Hyperactivity Disorder and Attention Deficit Disorder with a game-like video display being used to obtain a measure of various neuropsychologic indicia of attention.

66 Claims, 27 Drawing Sheets

OTHER PUBLICATIONS

Bruce, et al.; "Effects of Sympathetic Nervous System Activation and Psychological Stress on Glucose Metabolism and Blood Pressure in Subjects with Type 2 Non–Insulin–Dependent Diabetes Mellitus"; Diabetologia; 35(9); 835–843; DIALOG: File 5, Acc# 08, 1992.*

Furnham, et al.; "Measuring Locus of Control: a Critique of General, Children's Health–and Work–related Locus of Control Questionaires"; British Journal of Psychology; v84 n4; p. 443(37); DIALOG: File 88, Acc# 03243301, Nov. 1993.*

Villa, et al.; "A Structured Pictorial Questionaire to Assess DSM–III–R–based Diagnosis in Children (6–11 years)"; Journal of Abnormal Child Psychology; v22 n4; p. 403(21); DIALOG: File 88, Acc# 03485678, Aug. 1994.*

Dialog Abstract: File 155, Acc# 0353751; Kennedy et al.; "Television Computer Games: A 'New Look' in Performance Testing"; Aviat Space EnViron Med); 5391; pp. 49–53, Jan. 1982.*

Adilman; "Videogames: Knowing the Score"; Creative Computing; v9; p. 224(5); DIALOG: File 148, Acc# 01891055, Dec. 1983.*

Mims; "Psychological Testing"; Computers & Electronics; v23; p. 22(6); DIALOG: File 47, Acc# 2654858, Feb. 1985.*

* cited by examiner

SCRIPT ENTRY SCREEN

SCRIPT NAME: DIABETES SCRIPT 1

| QUERIES | CHOICE 1 | CHOICE 2 | CHOICE 3 | CHOICE 4 |
|---|---|---|---|---|
| HOW DO YOU FEEL? | VERY BAD | BAD | GOOD | VERY GOOD |
| HOW WELL ARE YOU MANAGING YOUR DISEASE? | VERY BADLY | BADLY | WELL | VERY WELL |
| HOW HARD IS IT FOR YOU TO FOLLOW YOUR TREATMENT PLAN? | VERY HARD | HARD | EASY | VERY EASY |
| HOW HARD IS IT FOR YOU TO CONTROL YOUR BLOOD SUGAR? | VERY HARD | HARD | EASY | VERY EASY |

SELECT DEVICE TYPE(S)

☒ GLUCOSE METER ☐ RESPIRATORY FLOW METER ☐ BP CUFF

CONNECTION TIME: 03:00 ▷

[ CREATE SCRIPT ] [ CANCEL ]

*Fig. 205*

NUMBER: 9001 {LF}
LED: 1 {LF}
ZAP: {LF}
CLS: {LF}
DISPLAY: ANSWER QUERIES NOW?
    PRESS ANY BUTTON TO START {LF}
WAIT: {LF}
CLS: {LF}
DISPLAY: HOW DO YOU FEEL?
    VERY                    VERY
    BAD      BAD     GOOD   GOOD {LF}
INPUT: 0000 {LF}
CLS: {LF}
DISPLAY: HOW WELL ARE YOU
    MANAGING YOUR DISEASE?
    VERY                    VERY
    WELL    BADLY    WELL   WELL {LF}
INPUT: 0000 {LF}
CLS: {LF}
DISPLAY: HOW HARD IS IT FOR YOU TO
    FOLLOW YOUR TREATMENT PLAN?
    VERY                    VERY
    HARD     HARD    EASY   EASY {LF}
INPUT: 0000 {LF}
CLS: {LF}
DISPLAY: HOW HARD IS IT FOR YOU TO
    CONTROL YOUR BLOOD SUGAR?
    VERY                    VERY
    HARD     HARD    EASY   EASY {LF}

*Fig. 206A*

```
INPUT: 0000 {LF}
CLS: {LF}
DISPLAY: CONNECT GLUCOSE METER
         AND PRESS ANY BUTTON
         WHEN FINISHED {LF}
WAIT: {LF}
CLS: {LF}
DISPLAY: COLLECTING MEASUREMENTS {LF}
COLLECT: GLUCOSE_METER {LF}
CLS: {LF}
DISPLAY: CONNECT APPARATUS TO
         TELEPHONE JACK AND
         PRESS ANY BUTTON
         WHEN FINISHED {LF}
WAIT: {LF}
LED: 0 {LF}
CLS: {LF}
DELAY: 03:00 {LF}
DISPLAY: CONNECTING TO SERVER {LF}
CONNECT: {LF}
{EOF}
```

*Fig. 206B*

PATIENT REPORT ~2058

PATIENT: LINDSEY, DAN ▷

~2042

QUERY RESPONSES

HOW DO YOU FEEL? BAD

HOW WELL ARE YOU
MANAGING YOUR DISEASE? BADLY

HOW HARD IS IT FOR YOU TO
FOLLOW YOUR TREATMENT PLAN? VERY HARD

HOW HARD IS IT FOR YOU TO
CONTROL YOUR BLOOD SUGAR VERY HARD

DATE OF MEASUREMENT: MARCH 15, 1997 ▷

~2116

MG/DL 160
150
140
130
120
110
100
90
80
70
60
50

6  8  10  12  14  16  18  20  22  24
HOURS

REMOTE PSYCHOLOGICAL DIAGNOSIS AND MONITORING SYSTEM

RELATED APPLICATIONS

This application is a continuation-in-part of U.S. patent application No. 09/127,404 filed Jul. 31, 1998, which is a continuation of U.S. patent application Ser. No. 08/843,495 which was filed Apr. 16, 1997 and issued on Oct. 27, 1998 as U.S. Pat. No. 5,828,943, and which is a file wrapper continuation of U.S. patent application Ser. No. 08/682,385 filed Jul. 17, 1996, now abandoned, which is a file wrapper continuation of U.S. patent application Ser. No. 08/479,570 filed Jun. 7, 1995, now abandoned, which is a file wrapper continuation of U.S. patent application Ser. No. 08/233,674 filed Apr. 26, 1994, now abandoned, priority from the filing date of which is hereby claimed under 35 U.S.C. §120, and all of which are hereby incorporated in their entirety by reference.

All the new subject matter in this continuation-in-part application comes from U.S. patent application Ser. No. 08/946,341, filed Oct. 7, 1997, which claims priority from provisional application No. 60/041,746 filed Mar. 28, 1997 and from provisional application No. 60/041,751 filed Mar. 28, 1997, priority from the filing date of which is hereby claimed under 35 U.S.C. §120, and all of which are incorporated herein by reference. For clarity, figure numbers and reference numerals from Ser. No. 08/946,341 have all been increased by a constant, respectively, in order to enable easier distinction as to the origin of the matter herein. Specifically, figure numbers have been increased by 200 and reference numerals by 2000.

FIELD OF THE INVENTION

This invention relates to apparatus and methods for diagnostic assessment of psychological conditions that enable a patient or user to collect important diagnostic measures of psychological conditions or behavior for transmittal to and analysis by a health care professional. The invention further relates generally to communication systems for remote monitoring of individuals, and in particular to a networked system for remotely monitoring individuals and for communicating information to the individuals through the use of script programs.

BACKGROUND OF THE INVENTION

The traditional method of diagnosing and assessing psychological conditions involves periodic clinical sessions in which a clinician attempts to obtain insights of a patient's condition by conducting interviews and, in some cases, conducting tests. This traditional method of psychological testing and evaluation is often very lengthy and, as a result, costly. Moreover, many psychological conditions and behavior patterns are not easily diagnosed during a series of routine clinical visits because the condition or behavior is situation-dependent and, thus, may not be observable in a clinical setting. Further, the manifestations or behavior patterns of certain disorders are heterogeneous in nature, which complicates identification and diagnosis. Specifically, where a high degree of heterogeneity is present, standardized and normalized diagnostic measures intended to identify a particular or preferred regimen of therapy often do not exist. Under such conditions, the identification and diagnosis of a psychological condition or behavior pattern becomes very subjective, often resulting in an even larger number of diagnostic clinical sessions and higher costs. Lower rates of diagnostic accuracy and efficacy also result.

Many people suffering from psychological disorders are unable to obtain clinical assistance because of the high cost of diagnosis and treatment. Further, even where cost is not of a major deterrent, many people lose confidence in the clinical procedure and cease attending clinical sessions when diagnostic assessment becomes difficult and lengthy. Difficulties can be encountered even by patients that persevere. Between their periodic clinical visits, they usually are left on their own with no encouragement or treatment.

Advances in the various fields of electronics and telecommunications have had a significant impact on medical diagnostic and monitoring equipment, including the development of devices that can be used in the home or other non-clinical settings. Recent advancement with respect to self-care health monitoring of afflictions such as diabetes were set forth in my patent application Ser. No. 07/977,323, filed Nov. 17, 1992, entitled "MODULAR MICROPROCESSOR-BASED HEALTH MONITORING SYSTEM" now issued as U.S. Pat. No. 5,307,263.

Some experiments and trials have been conducted with respect to incorporating computers and similar electronic equipment in arrangements for psychological testing and assessment that is performed in a clinical setting. Very recently, some experiments and trials have been conducted in which a patient uses a microprocessor device such as a "palm-top computer" to record behavioral information between clinical sessions and, in some cases, for limited therapeutic purposes. However, adoption of modem microprocessor and communication technology to diagnosing, monitoring or treating psychological disorders has not progressed at the same rate as technological advances in areas of medicine that relate to physiological conditions.

There are numerous reasons why microprocessors and modem communication techniques have not been widely applied to devices for psychological diagnoses, evaluation or treatment. As previously mentioned, the behavior attendant many psychological disorders is situation dependent. Thus, to be useful, a device must be relatively small, relatively easy to use and unobtrusive so that a patient or subject can use the device in an appropriate environment and is comfortable with using the device in that environment. Cost and efficacy are also important factors if use of the device is to result in a reduction in the professional time and other costs associated with diagnosis and treatment of various psychological conditions.

In order to provide a diagnostic tool that can be used in settings other than clinical sessions, other criteria should be met. For example, provision should be made for a clinician or other health care professional to easily acquire data gathered by the diagnostic tool and to analyze that data. Further, to achieve optimum utilization, the diagnostic tool should be extremely versatile, lending itself to adaptation to the assessment of various psychological conditions. Preferably, the device should be adaptable enough to allow a clinician to establish diagnostic routines suited for various species of the same general psychological disorder of even for a particular individual. Versatility sufficient for use of the device in at least limited monitoring and therapeutic procedures is also desirable.

For all of the above reasons, a need exists for improved methods and apparatus for psychological evaluation and assessment. This is especially true with disorders such as depression, anxiety, schizophrenia, addiction, eating disorders, attention deficit disorders, attention deficit and hyperactivity disorder, and other psychological and behavioral problems which are highly stimulus-dependent (i.e., may be manifested primarily or only in situations that are difficult to synthesize in a clinical environment). The extreme heterogeneity of these psychological conditions has complicated diagnosis and treatment, a drawback that leaves many adults and children with chronic conditions that are handicaps both from the social and economic standpoint.

Providing reliable and accurate tests for diagnosing psychological disorders in children has been a substantial problem. In particular, prevalent childhood psychological disorders such as Attention Deficit Hyperactivity Disorder and Attention Deficit Disorder are difficult to assess because attention is a multi-construct neuropsychological process that includes sustained attention (vigilance) and selective attention (i.e., the ability to maintain attention in the presence of distractions and the ability to appropriately shift attention). Children with Attention Deficit Disorder and Attention Deficit and Hyperactivity Disorder are often impulsive, requiring a relatively high degree of motivation in order to complete tasks that employ cognitive skills appropriate to their particular age group. Moreover, current assessment tests for Attention Deficit Disorder and Attention Deficit Hyperactivity Disorder are relatively subjective, and even when effectively administered, basically provide only an evaluation of whether a child exhibits a deficit in his or her ability to focus and maintain attention. That is, current tests have been successful only in identifying a large heterogeneous group that exhibit the basic symptoms of Attention Deficit Hyperactivity Disorder. Little success has been obtained relative to assessing the degree of neuropsychologic mechanism impairment. Thus, current diagnostic techniques do not identify homogeneous subgroups of children having Attention Deficit Hyperactivity Disorder, which is needed in order to prescribe and administer effective therapy.

Developing diagnostic and therapeutic tools for psychological assessment and treatment of children is especially challenging. To obtain essential, unbiased information for diagnosis of Attention Deficit Hyperactivity Disorder or Attention Deficit Disorder, a child being tested must be at ease and must be motivated since children with these disorders are easily distracted when faced with situations requiring continued attention and/or routine, relatively tedious tasks. Thus, if cognitive tests are employed, they must be appealing to younger children, but not leave older children bored and unmotivated to perform well. Otherwise, test results will be skewed and diagnosis made even more difficult.

In the United States alone, over 100 million people have chronic health conditions, accounting for an estimated $700 billion in annual medical costs. In an effort to control these medical costs, many healthcare providers have initiated outpatient or home healthcare programs for their patients. The potential benefits of these programs are particularly great for chronically ill patients who must treat their diseases on a daily basis. However, the success of these programs is dependent upon the ability of the healthcare providers to monitor the patients remotely to avert medical problems before they become complicated and costly. Unfortunately, no convenient and cost effective monitoring system exists for the patients who have the greatest need for monitoring, the poor and the elderly.

Prior attempts to monitor patients remotely have included the use of personal computers and modems to establish communication between patients and healthcare providers. However, computers are too expensive to give away and the patients who already own computers are only a small fraction of the total population. Further, the patients who own computers are typically young, well educated, and have good healthcare coverage. Thus, these patients do not have the greatest unmet medical needs. The patients who have the greatest unmet medical needs are the poor and elderly who do not own computers or who are unfamiliar with their use.

Similar attempts to establish communication between patients and healthcare providers have included the use of the Internet and Internet terminals. Although Internet terminals are somewhat less costly than personal computers, they are still too expensive to give away to patients. Moreover, monthly on-line access charges are prohibitive for poor patients.

Other attempts to monitor patients remotely have included the use of medical monitoring devices with built-in modems. Examples of such monitoring devices include blood glucose meters, respiratory flow meters, and heart rate monitors. Unfortunately, these monitoring devices are only designed to collect physiological data from the patients. They do not allow flexible and dynamic querying of the patients for other information, such as quality of life measures or psychosocial variables of illness.

Prior attempts to monitor patients remotely have also included the use of interactive telephone or video response systems. Such interactive systems are disclosed in U.S. Pat. Nos. 5,390,238 issued to Kirk et al. on Feb. 14, 1995; 5,434,611 issued to Tamura on Jul. 18, 1995; and 5,441,047 issued to David et al. on Aug. 15, 1995. One disadvantage of these systems is that they either require a patient to call in to a central facility to be monitored or require the central facility to call the patient according to a rigid monitoring schedule.

If the patients are required to call the central facility, only the compliant patients will actually call regularly to be monitored. Non-compliant patients will typically wait until an emergency situation develops before contacting their healthcare provider, thus defeating the purpose of the monitoring system. If the central facility calls each patient according to a monitoring schedule, it is intrusive to the patient's life and resistance to the monitoring grows over time.

Another disadvantage of these conventional interactive response systems is that they are prohibitively expensive for poor patients. Further, it is difficult to identify each patient uniquely using these systems. Moreover, these systems are generally incapable of collecting medical data from monitoring devices, such as blood glucose meters, respiratory flow meters, or heart rate monitors.

OBJECTS AND ADVANTAGES OF THE INVENTION

In view of the above, it is an object of the present invention to provide a simple and inexpensive system for remotely monitoring patients and for communicating information to the patients. It is another object of the invention to provide a system which allows flexible and dynamic querying of the patients. It is a further object of the invention to provide a system which combines querying of patients with medical device monitoring in the same monitoring session. Another object of the invention is to provide a monitoring system which incurs lower communications charges than those incurred by conventional monitoring systems. A further object of the invention is to provide a monitoring system which may be used at any time convenient for a patient.

These and other objects and advantages will become more apparent after consideration of the ensuing description and the accompanying drawings.

SUMMARY OF THE INVENTION

This invention addresses the previously discussed need for new and useful apparatus and methods for diagnostic assessment of psychological conditions, providing a valuable adjunct and supplementation to traditional clinical assessment. Apparatus arranged in accordance with the invention is extremely versatile, being suitable for use in diagnostic assessment of various psychological conditions and being especially well suited for assessment of conditions that affect children such as Attention Deficit Disorder and Attention Deficit Hyperactivity Disorder. The invention also is extremely versatile in that it is suited for use in a clinical setting as well as use in remote locations such as the home, school, or workplace.

Basically, apparatus configured in accordance with the invention includes a programmable microprocessor unit that is responsive to program instructions that are supplied by an external source. In the disclosed embodiment, a receptacle is included in the programmable microprocessor-based unit for receiving an external ("removable/insertable") memory unit which includes a digital storage medium for storing program instructions that control operation of the programmable microprocessor-based unit. In other embodiments, the program instruction instructions can be transferred to memory circuits of the microprocessor-based unit by various digital data transmission systems and techniques.

The programmable microprocessor-based unit also includes circuitry for generating a video display in accordance with program instructions stored in an internal memory of the microprocessor-based unit and/or the digital storage medium of the external memory unit. In the operation of the invention, the displayed video signals interactively prompt a patient or user to operate one or more switches that are located on the microprocessor-based unit. Preferably, the programmable microprocessor-based unit also includes a sound generator operable for producing selected tones, single words or simple phrases of simulated speech, simple musical passages, and other sounds appropriate to the video display during the operation of the microprocessor-based unit.

In the currently preferred embodiments of the invention, the microprocessor-based unit is a compact video game system, with the program instructions being provided by an external memory unit that corresponds to a game cartridge. The invention can employ either a hand held video game such as the compact video game system manufactured by Nintendo of America Inc. under the trademark "GAME BOY," or less compact video game systems such as the "SUPER NES" video game, which also is marketed by Nintendo of America Inc. As is well known, hand held video games of the type mentioned are unitary devices that include a display screen and control switches for operating the video game. On the other hand, the larger video game systems operate in conjunction with a television set or video monitor and consist of a console unit, which receives a game cartridge, and one or more controllers, which include at least a portion of the switches for operating the video game system. Use of either type of video game system has several general advantages, including the widespread availability and low cost of such systems. Further, such systems provide an easy-to-use, unobtrusive device that can be used either in a clinical setting or other environment such as the home, school, or workplace. Moreover, the video display can be structured to provide motivation for a patient or user and, in at least some instances, the same or an additional program cartridge can provide appropriate educational or therapeutic video displays and processes.

Use of the video game system for the programmable microprocessor-based unit of the invention is especially advantageous with children because of the popularity and widespread acceptance of all types of video games. In accordance with the invention, video and audio sequences are preferably presented in game-like format with animation that is suitable for children or other selected age groups.

Regardless of whether a video game system is employed, the programmable microprocessor-based unit can be used to analyze the data obtained during a diagnostic assessment procedure. In some cases, a full analysis will be performed so that the information that is transmitted or returned to a clinician is in a final form. In other situations, partial (or even no) analysis of gathered diagnostic information is performed by the programmable microprocessor-based unit. In those situations, partial (or full) analysis is performed at the clinician's facility or, alternatively, at a facility that gathers information for analysis and subsequent relay to the clinician.

Systems that are arranged in accordance with the invention include two components in addition to the above-discussed programmable microprocessor-based unit: (1) a programmable digital signal processor; and, (2) a communication link for allowing signal transmission between the programmable microprocessor-based unit and the programmable digital signal processor. In some arrangements of the invention, the programmable digital signal processor is a personal computer that is located at the clinic or other facility of the health care professional. In these arrangements, the programmable microprocessor-based unit can be located at the clinician's facility with the communication link for coupling signals between the programmable microprocessor-based unit and the clinician's computer being an electrical cable that provides a RS232 communication link or some other digital signal transmission arrangement. However, a primary advantage of the invention is use of the microprocessor-based unit at a location that is remote from the clinician's facility (e.g., use between clinical sessions in an environment appropriate to assessment of the psychological condition of interest). At least two basic types of communication links allow assessment of the psychological condition to be made at a subject's home or other location that is remote from the clinician's facility.

First, an RS232 serial data port or other means for coupling digital signals to the central processing unit of the clinician's personal computer can be connected to a cable that is adapted for receiving an external memory unit (e.g., memory cartridge) that is used with the programmable microprocessor-based unit to gather assessment data. In such an arrangement, the external memory unit is interconnected with the clinician's computer to access stored signals that represent information gathered during a diagnostic assessment procedure that was performed earlier at a subject's home or other suitable location. In many situations, the clinician's computer will have been previously interconnected with the external memory unit to allow the clinician to establish stored program instructions that will implement a desired diagnostic assessment procedure when the patient or user operates the microprocessor-based unit in conjunction with the memory unit.

The second type of communication link that allows the diagnostic assessment procedure to be conducted at a location other than the clinician's facility involves the use of various types of signal transmission media. For example, the digital data signal processor (e.g., personal computer) employed by the clinician can include an external or internal modem for receiving and transmitting digital signals via the various types of conventional telephone systems. Likewise, a modem and associated conventional data management circuitry can be either included in or interconnected with the microprocessor-based unit to allow information gathered during a diagnostic assessment procedure to be transmitted to the clinician for review and analysis. In some cases, it may also be advantageous to use the data transmission link for remote programming of the user's external memory unit, thereby permitting changes to be made in the diagnostic procedure of a particular patient or user without a visit to the clinician's office.

Transmission media other than a telephone system can be used for coupling signals between a clinician's digital data processing system and a remotely located programmable microprocessor-based unit that is used for diagnostic assessment of psychological conditions. For example, recently developed interactive audio/visual systems using coaxial cable or optical fiber can be employed as well as other types of digital networks that provide information services and communication between users. In some of these arrangements, the digital data signal processor need not be located at the clinician's facility. That is, the invention can be implemented so that the digital signal processor is a clearinghouse that in effect functions as a central server that is capable of functioning with a relatively large number of programmable microprocessor units and, in addition, capable of serving the needs of at least several clinicians. In these arrangements, the clearinghouse digital signal processor collects and stores diagnostic assessment information transmitted to the clearinghouse from any number of programmable microprocessor-based units. Information is then provided to the appropriate clinician or clinical facility by facsimile or data transmission techniques. Alternatively, the information can be printed and delivered to the appropriate clinician.

The disclosed embodiments of the invention are configured and programmed for diagnostic assessment of Attention Deficit Disorder and Attention Deficit Hyperactivity Disorder. The currently preferred realizations of the disclosed embodiment allow a clinician to selectively configure sequences of tests ("tasks") that fall into the two basic categories: delay reaction tasks and performance-paced continuous performance tasks. During a delay reaction task, the programmable microprocessor-based unit operates to first generate an audible and/or visual warning signal to alert the user that the microprocessor-based unit will soon produce an audio, visual, or audiovisual target stimulus. When the target stimulus is produced, the user or patient responds by activating a switch or control of the microprocessor-used unit. Preferably, the time between the warning stimulus and the target stimulus within a predetermined range that is selected by the clinician, with each particular time delay being randomly selected through programmed operation of the microprocessor-based unit. For each delayed reaction task, a signal is generated indicating whether the user reacted to the target stimulus and, if so, the time that elapsed between generation of the target stimulus and the user's operation of the selected switch. Collecting and storing the user's reaction times for a sequence of delayed reaction tasks allows subsequent analysis by the system digital data processor to obtain information such as a record of reaction time versus time delay, the user's best (fastest) reaction time, the user's mean reaction time, and/or the standard deviation of reaction times. In some situations, it may also be advantageous to store the delayed reaction task information so that analysis can be performed that allows the detection of trends such as whether the user's reaction time generally increased or decreased as the sequence of delayed reaction tasks progressed. Such information may indicate an increase or decrease in attention level with time.

In the currently preferred realizations of the disclosed embodiment of the invention, the visual delayed reaction task includes the display of a car, the model of which selected by the user prior to initiation of the diagnostic procedure. The car is shown at a starting line with a traffic signal having a red, yellow, and green light being prominently displayed in the foreground. Initially, the red light is illuminated, a warning signal is then provided to the user by illuminating the yellow light and, when the microprocessor-selected time delay has elapsed, the green light is illuminated to provide the target stimuli. In the currently preferred realizations of the disclosed embodiments of the invention, the words "ready . . . set . . . go" are synthesized by the sound generator of the microprocessor-based unit.

During the continuous performance tasks, the system user observes the system display while target stimuli pass across it. The object is for the user to activate a switch or control of the microprocessor-based unit when target stimuli are at a predetermined location on the display. For example, in the currently preferred realizations of the disclosed embodiments of the invention, the previously mentioned car is displayed so that it appears to be passing by trees that are located along the side of a road. The target stimulus is a specified type of fruit (e.g., an orange, apple, lemon, or cluster of grapes) on the tree. The object is for the user to activate the switch or control of the microprocessor-based unit when a predetermined stimulus appears (e.g., an apple). When the switch or control is activated a hand and arm move upwardly from the car and, if the switch is timely activated, the fruit is captured. When the user correctly identifies and captures a target stimulus, the time interval between appearance of target stimuli is decreased by a predetermined amount. On the other hand, if the user does not properly respond to a target stimulus, the time interval between target stimuli is increased.

During the conduction of a sequence of continuous performance tasks, information is recorded to reflect the number of target stimuli correctly identified, the number of target stimuli missed, the number of responses to non-target stimuli, the number of correct, but delayed, responses, and the final interstimulus time interval.

Audio continuous performance tasks are also provided wherein the user is to respond to certain audio signals while ignoring others. For example, in the currently preferred realizations of the disclosed embodiments, the car shown on the system display unit is passing along a dark road with a small portion of the road passing under the car's headlights. A low frequency "radar beep" is sounded for each non-target stimulus, and a high frequency radar beep is sounded to represent the target stimulus. Although the display is relatively dark, the bases of the trees can be seen and when the user properly responds to a target stimulus, a hand swings upwardly from the car to catch the fruit.

The battery of tests provided by the currently preferred embodiments of the invention also include continuous performance tasks with various distractions. For example, in the above-discussed realization in which the user activates a switch or control of the microprocessor-based unit to catch a predetermined type of fruit as a car passes across the system display, moving objects such as hopping frogs, fluttering butterflies, and flying saucers are periodically and randomly displayed. In the audio continuous performance tasks, the distractions consist of synthesized speech such as "Now!" or "Go!." During sequences of continuous performance tasks that include distractions, the number of distractions that cause user reaction are recorded as well as the information recorded during continuous performance task sequences that do not include distractions.

SUMMARY—I

The invention presents a networked system for remotely monitoring an individual and for communicating information to the individual. The system includes a server and a remote interface for entering in the server a set of queries to be answered by the individual. The server is preferably a world wide web server and the remote interface is preferably a personal computer or network terminal connected to the web server via the Internet. The system also includes a remotely programmable apparatus for interacting with the individual. The apparatus is connected to the server via a communication network, preferably the Internet. The apparatus interacts with the individual in accordance with a script program received from the server.

The server includes a script generator for generating the script program from the queries entered through the remote interface. The script program is executable by the apparatus to communicate the queries to the individual, to receive responses to the queries, and to transmit the responses from the apparatus to the server. The server also includes a database connected to the script generator for storing the script program and the responses to the queries.

The apparatus has a communication device, such as a modem, for receiving the script program from the server and for transmitting the responses to the server. The apparatus also has a user interface for communicating the queries to the individual and for receiving the responses to the queries. In the preferred embodiment, the user interface includes a display for displaying the queries and user input buttons for entering the responses to the queries. In an alternative embodiment, the user interface includes a speech synthesizer for audibly communicating the queries and a speech recognizer for receiving spoken responses to the queries.

The apparatus also includes a memory for storing the script program and the responses to the queries. The apparatus further includes a microprocessor connected to the communication device, the user interface, and the memory. The microprocessor executes the script program to communicate the queries to the individual, to receive the responses to the queries, and to transmit the responses to the server through the communication network.

In the preferred embodiment, the system also includes at least one monitoring device for producing measurements of a physiological condition of the individual and for transmitting the measurements to the apparatus. The apparatus further includes a device interface connected to the microprocessor for receiving the measurements from the monitoring device. The measurements are stored in the memory and transmitted to the server with the responses to the queries. The server also preferably includes a report generator connected to the database for generating a report of the measurements and responses. The report is displayed on the remote interface.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 205 is a script entry screen according to the preferred embodiment of the invention;

FIG. 206A is a listing of a sample script program according to the preferred embodiment of the invention;

FIG. 206B is a continuation of the listing of FIG. 206A;

FIG. 210 is a sample report displayed on a workstation of the system of FIG. 201;

DETAILED DESCRIPTION OF THE PREFERRED EMBODIMENT

Figure 1:
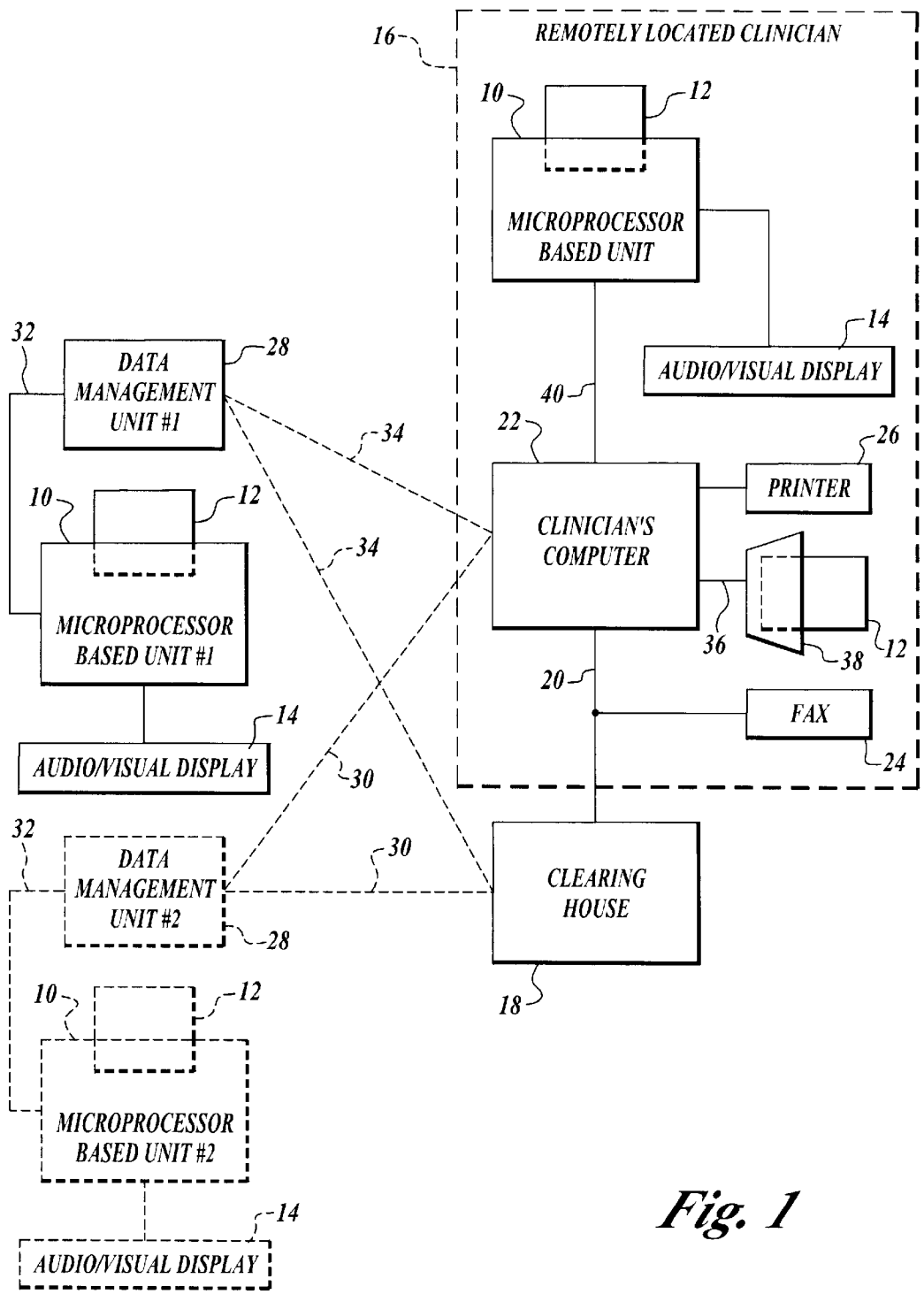
FIG. 1 is a block diagram that illustrates a psychological diagnostic measurement system of this invention, depicting microprocessor-based patient units connected in signal communication with a clinician's computer system and/or a clearinghouse for collection and analysis of diagnostic data originating with a large number of patient units.

FIG. 1 illustrates one embodiment of a diagnostic measurement system configured in accordance with the invention. The depicted embodiment includes a programmable microprocessor-based unit 10 that includes a receptacle for receiving an external memory unit 12, which can be easily inserted and removed from microprocessor-based unit 10. Removable memory unit 12 includes a digital storage medium for storing program instructions that control the operation of microprocessor-based unit 10 and, in addition, allows storage of diagnostic test information that is generated during operation of microprocessor-based unit 10 for diagnostic assessment of a psychological condition.

Various storage media known to those skilled in the art can be used as the digital storage medium of external memory unit 12. For example, conventional read-only memory (ROM) can be employed for storage of program instructions that are not changed or altered when external memory 12 is reconfigured for a different patient or reconfigured for measurements relating to a different type of psychological condition. Optically scanned memory such as currently available compact disc memory can also be employed. In addition, various types of erasable read-only memory and random access memory (RAM) having a battery back-up can be used to provide a storage medium for program instructions that may be changed when external memory 12 is configured for use with a different patient or for the diagnostic assessment of the different psychological condition. Erasable read-only memory or battery backed-up RAM also can be used for storage of information gathered when microprocessor-based unit 10 is operated to gather diagnostic measurement information that relates to one or more psychological conditions. Moreover, in newly developing technologies such as audio/video interactive television and networks for digital communications program instructions can be transmitted to microprocessor-based unit 10 and stored in random access memory.

As is indicated in FIG. 1, microprocessor-based unit 10 is interconnected with an audio/visual display unit 14. During operation of the invention for diagnostic assessment of psychological conditions, microprocessor-based unit 10 generates audio and video signals that are presented to the patient or system user by audio/visual display unit 14. The audio/visual presentation is controlled by program instructions that are either stored in external memory 12 or are otherwise supplied to microprocessor-based unit 10. In the disclosed embodiments, the visual presentation is structured to elicit responses from the user of microprocessor-based unit 10 (e.g., a patient or research subject) that provide that diagnostic measures relating to a particular psychological condition. In that regard, the embodiments disclosed herein are arranged for diagnostic assessment of Attention Deficit Hyperactivity Disorder and Attention Deficit Disorder. Upon understanding the operation of the invention and the various manners in which it can be configured, it will be recognized that the invention can be used in the diagnoses of various other psychological conditions and behavior patterns, including anxiety disorders, depression, schizophrenia, addiction, and weight control/eating disorders.

A primary advantage of the invention is the ability to conduct a diagnostic assessment procedure in an environment other than the office of a clinician or other health care facility. This particular aspect of the invention can be important with respect to diagnosing psychological conditions that are highly situation-dependent. Further, since it is not necessary for a clinician to be present when a diagnostic assessment procedure is executed, the costs of diagnoses and treatment is reduced. For example, during a clinical session, a clinician can instruct a patient or subject in the use of the invention for diagnostic assessment of a particular psychological condition. The patient or user then uses microprocessor-based unit 10, a suitably programmed external memory 12, and an audio/visual display unit 14 between clinical sessions to gather appropriate diagnostic measurements while the subject is in suitable environmental surroundings (e.g., at home, school, or the workplace). Information gathered during the diagnostic assessment is then made available to the clinician for consideration and analysis.

There are two basic ways in which information that relates to the results of the diagnostic assessment can be conveyed to a clinician or other person who serves as an administrator for the conduction of the diagnostic assessment. These same techniques are employed for establishing the diagnostic procedure (i.e., storing suitable program instructions in external memory 12). The first technique for transferring test results or programming microprocessor-based unit 10 (e.g., external memory unit 12) involves data transmission between microprocessor-based unit 10 and a remotely located clinician's office (or other health care facility) or, alternatively, a remotely located facility that stores the information for subsequent analysis and transmission to the clinician. In the second technique, microprocessor-based unit 10 (or external memory unit 12) is physically transferred between the site at which the diagnostic assessment is made and the clinician's facility or other remote location.

With respect to the first information transfer technique, FIG. 1 schematically illustrates arrangement of the invention for remote exchange of data and information between a microprocessor-based unit 10 and either a remotely located clinician 16, or a clearinghouse 18. In such an arrangement, clearinghouse 18 includes one or more digital signal processors and associated peripheral equipment (e.g., printers, signal storage media, facsimile facilities) sufficient for gathering diagnostic measurement information from a relatively large number of microprocessor-based diagnostic tools (represented by microprocessor-based unit number 1 and microprocessor-based unit number 2 of FIG. 1). A communication link 20 is shown in FIG. 1 between clearinghouse 18 and the clinician's remote location 16 to indicate transfer of information electronically or by other signal transmission means. Specifically, data and information can be transferred electronically between clearinghouse 18 and a clinician by various conventional data transmission systems, including those implemented through telephony, transmission of radio frequency signals, modulated coherent light, etc. As is indicated in FIG. 1, the signals sent by clearinghouse 18 to the clinician's facility 16 can be coupled to devices such as the clinician's computer 22 and/or the clinician's facsimile machine 24. Signals transmitted to the clinician's computer 22 can be stored with or without additional processing. In the same regard, analytical signal processing of the diagnostic assessment data gathered by microprocessor-based unit can be performed at various stages of information transmission between patient and clinician. For example, data processing can be performed in microprocessor-based unit 10, the clinician's computer 22, clearinghouse 18 and/or the hereinafter described data management unit 28. In any case, when the diagnostic information is transmitted to the clinician's facility, it can be displayed on a display unit of the clinician's computer 22 (not shown in FIG. 1); printed by a printer 26 that is connected to computer 22; or processed by other devices that are peripheral to the clinician's computer 22.

With continued reference to the embodiment of the invention shown in FIG. 1, signals representative of information gathered during a diagnostic assessment procedure (and other signals appropriate to system operation) are coupled to (or from) clearinghouse 18 and microprocessor-based diagnostic unit 10 via a data management unit 28 and a communication link 30. Like communication link 20, which provides signal transfer between clearinghouse 18 and the clinician's facility 16, communication link 30 can be of several different types. In some instances, communication link 30 will be a signal path established by a telephone system. Alternatively, RF signal transmission can be employed. Communication link 30 also can be established through the use of specialized digital networks, including recently developed interactive audio/video systems such as those operated in conjunction with cable television.

In the arrangement of FIG. 1, each depicted data management unit 28 is interconnected with its associated microprocessor-based unit 10 by a cable 32 that includes electrical conductors for carrying signals between the two units. In each arrangement of the invention, data management unit 28 provides the signal processing that is necessary for interfacing microprocessor-based unit 10 with communications link 30 and/or a communications link 34. Communications link 34 provides for transmission of signals between microprocessor-based unit 10 and the clinician's remote location 16 (e.g., coupling of signals to and from the clinician's computer 22). Like the previously discussed communication links 20 and 30, communication link 34 can be realized in a variety of ways.

Because of the wide range of communication links 30 and 34 that are available for practice of the invention, data management 28 will take on various forms and configurations. For example, in an arrangement of the invention in which communications link 30 and/or 34 is a signal path established by a conventional telephone system, data management unit 28 will include a modem and will operate to perform the signal processing necessary to transmit information to clearinghouse 18 and/or the clinician's remote location 16. In some arrangements of the invention, the signal processing required for modem data transmission will be implemented by a microprocessor unit that is incorporated in data management unit 28. In other situations, the microprocessor of microprocessor-based unit 10 can be employed to perform the signal processing necessary for modem signal transmission. Similarly, the hardware associated with modem transmission (e.g., telephone line connection) can be included in data management unit 28 or incorporated in microprocessor-based unit 10.

FIG. 1 also indicates one manner in which the invention can be employed for remote administration of diagnostic assessment of psychological conditions without the need for data management unit 28 and communication links 30 and 34. In particular, in the arrangement of FIG. 1, an external memory unit 12 can be inserted in a receptacle 38 that electrically connects external memory unit 12 to the clinician's computer 22 via a cable 36. With an external memory 12 connected in this manner, a clinician or other administrator of the diagnostic assessment to be performed can operate computer 22 to store program instructions appropriate for the diagnostic procedure in an external memory unit 12. The programmed external memory unit 12 can be given to a patient or subject at the end of a clinical session or transmitted to the patient or subject by other appropriate means. The patient or subject can subsequently insert the programmed external memory unit 12 in a microprocessor-based unit 10 that is located at the patient's home or some other location at which the diagnostic procedure will be executed. Signals representative of the diagnostic information gathered during the procedure are stored in external memory unit 12 when microprocessor unit 10 implements the diagnostic assessment procedure. External memory unit 12 is then returned to the clinician, inserted into receptacle 38 and the clinician's computer 22 is used to retrieve the diagnostic information stored in the external memory unit 12. In situations in which program instructions and diagnostic results are stored internally in microprocessor-based unit 10 (i.e., without use of an external memory unit 12), the entire microprocessor-based unit can be taken to the clinician's office. Information relating to diagnostic assessment results can then be unloaded to the clinician's computer 22 and, if desired, program instructions can be downloaded to the microprocessor-based unit 10 for administering further diagnostic assessment.

As also is shown in FIG. 1, in most applications of the invention, an additional microprocessor-based unit 10 and audio/visual display unit 14 will be located at the clinician's office or other facility. In the arrangement shown in FIG. 1, the additional microprocessor-based unit 10 is directly connected to the clinician's computer 22 by an electrical cable 40 to allow signal transmission between the microprocessor-based unit and computer 22. Providing a microprocessor-based unit 10 and audio/visual display unit 14 at the clinician's location allows a patient or subject to be instructed in the use of the system and also allows the administration of diagnostic assessment procedures at the clinician's facility, if desired.

Figure 2:
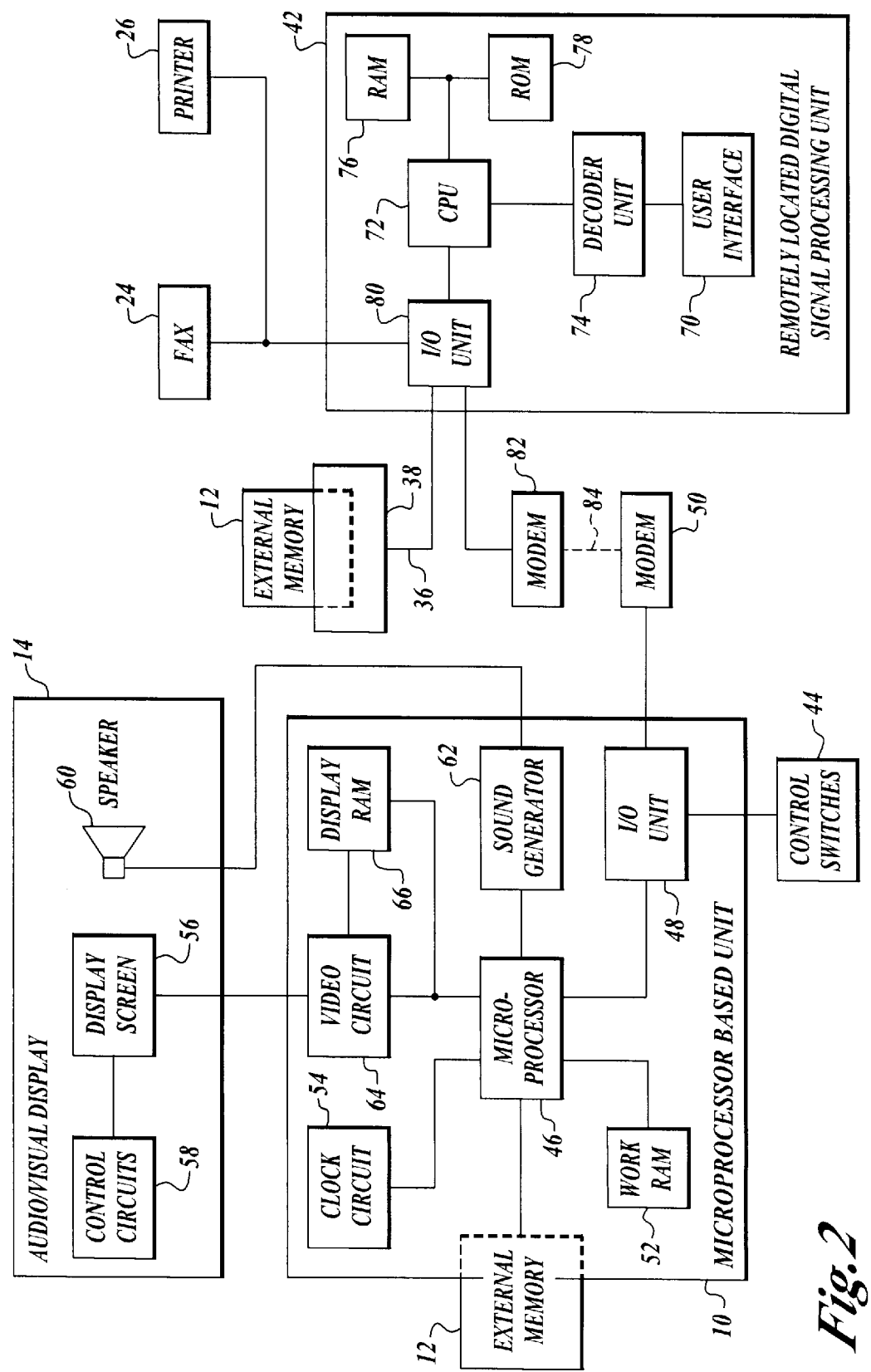
FIG. 2 is a block diagram illustrating in greater detail the basic structure of a microprocessor-based patient unit and a digital signal processor of a type that can be used within a clearinghouse or be used as a clinician's computer.

FIG. 2 depicts a more detailed block diagram of a microprocessor-based unit 10 that can be employed in the practice of the invention and an associated audio/visual display unit 14. Also shown in FIG. 2 is a basic block diagram of a remotely located digital signal processing system 42 which typifies the arrangement of clearinghouse 18 and computer 22 of FIG. 1.

As is indicated in FIG. 2, signals supplied by one or more control switches 44 are coupled to a microprocessor 46 of microprocessor-based unit 10 via an input/output circuit 48. Also interconnected with input/output unit 48 of microprocessor-based unit 10 is an external modem 50, which serves as data management unit 48 (FIG. 1) for the depicted arrangement. Although not indicated in FIG. 2, it will be understood by those skilled in the art that interconnections such as the connection shown between microprocessor 46 and input/output unit 48, generally include a data, address, and control bus.

With continued reference to microprocessor-based unit 10 of FIG. 2, the depicted microprocessor 46 is interconnected with the receptacle that receives an external memory unit 12 so that microprocessor 46 can access program instructions stored in external memory unit 12 and store diagnostic assessment results in external memory 12. As previously mentioned, program instructions can be provided to a microprocessor-based unit 10 via a digital signal communications system, instead of an external memory unit 12. In such arrangements, digital signals supplied by a system such as cable television or a digital communications can be coupled to microprocessor 46 via input/output unit 48 or other conventional signal processing arrangements.

In the arrangement of FIG. 2, a random access memory 52 is interconnected with and is used by microprocessor 46 to implement a desired diagnostic assessment procedure and perform any desired analysis of the gathered diagnostic data. In addition, random access memory 52 can be used for storing program instructions that are supplied to an embodiment of the invention that does not employ an external memory unit 12 (i.e., an embodiment in which program instructions are supplied via a digital signal communications system). A clock circuit 54 is provided to allow microprocessor 46 to store date and time signals in situations in which date and time tags are to be included with the gathered diagnostic data. Although not specifically shown in FIG. 2, microprocessor-based unit 10 generally includes an internal read-only memory for storing various program instructions and data that are not unique to a particular diagnostic assessment procedure or other application for the microprocessor-based unit 10.

The audio/visual display unit 14 that is shown in FIG. 2 corresponds to a video monitor that includes a display screen 56, control circuitry 58, and a speaker 60. In an arrangement of this type, microprocessor 46 of microprocessor-based unit 10 controls the operation of a sound generator 62 and video circuits 64 in accordance with the program instructions stored in external memory 12. A display random access memory 66 is used to store and format video signals which are coupled to display screen 56 of audio/visual display unit 14. Music, synthesized speech, and other sounds generated by sound generator 62 are coupled to speaker 60. Control circuit 58 includes the circuitry necessary for adjusting volume and display quality as well as the circuitry for driving the display screen. In other arrangements, a television set may be used as audio/visual display unit 14, with microprocessor-based unit 10 supplying an appropriate modulated RF signal or being connected to the television set video and audio inputs.

It will be recognized by those of ordinary skill in the art that a diagnostic tool that corresponds to microprocessor-based unit 10 of FIGS. 1 and 2 can be easily realized using conventional microprocessor design techniques and components. It also will be recognized that various commercially available devices can be adopted for use as a microprocessor-based unit 10 of this invention. In that regard, in the currently preferred embodiments of the invention, the microprocessor-based unit 10 is a compact video game system, with external memory unit 12 being configured to correspond to the type of game cartridge that is used with that particular video game system. In some arrangements of the invention, a hand held video game system such as the compact video game system marketed by Nintendo of America Inc. under the trademark "GAME BOY" can be used to realize, in unitary form, microprocessor-based unit 10, audio/visual display unit 14, and control switches 44 of the arrangement shown in FIG. 2. In other applications of the invention, a less compact video game system such as the "SUPER NINTENDO ENTERTAINMENT SYSTEM" or "NES" video game is used. In those situations, control switches 44 correspond to the video game controller and audio/visual display unit 14 is a conventional television set or video monitor. The less compact video game systems often are advantageous because the external memory unit (game cartridge) has greater memory capacity than the corresponding memory of hand held units; the microprocessor has superior processing capability; and relatively high-quality sound and graphics can be achieved.

Regardless of the type employed, there are many advantages to using a video game system in the practice of the invention. Of prime importance, video game systems enjoy widespread popularity and, hence, low cost. In many cases, the user of a diagnostic assessment system that is constructed in accordance with the invention may already own or have access to a video game system. In addition, video game systems are simple to use. Therefore, little time is required for instructing a patient or other system user in how to operate the system for performance of a particular diagnostic assessment. Even further, adapting a video game system for use with the invention provides a convenient way for realizing diagnostic assessment procedures that are presented in game-like format with animation or other graphics that provide motivation for all age groups while gathering needed diagnostic data. The cumulative effect is achievement of an unobtrusive test and diagnosis arrangement that is acceptable to patients and other subjects and can be used in many environments.

Referring again to FIG. 2, it can be recognized that the depicted remotely located digital signal processing unit 42 corresponds to a wide range of computational arrangements, including the clinician's computer 22 of FIG. 1 and the previously discussed, more complex, clearinghouse 18 of FIG. 1. In the arrangement depicted in FIG. 2, a user interface 70 is connected in signal communication with a central processor unit 72 via a decoder circuit 74. Random access memory 76 and read-only memory 78 are accessed by central processor unit 72 of digital signal processing unit 42 during execution of the various programs and procedures used in carrying out the invention. An input/output unit 80 acts under the direction of central processor unit 72 to provide signals to a facsimile unit 24 and printer 26. As also is indicated in FIG. 2, signals can be provided to central processor unit 72 via input/output unit 80 by a modem 82. In the arrangement shown, a communication link 84 interconnects modem 82 with modem 50 to thereby allow the depicted digital signal processing system to receive diagnostic test information from the depicted microprocessor-based unit 10. As also is indicated, input/output unit 80 is connected to a receptacle 38, which as was described relative to FIG. 1, allows the digital data processing system to access storage addresses within an external memory unit 12 that is connected to receptacle 38. As shall be described in more detail, an administration program that is executable by digital signal processing unit 42 includes a program module that allows program instructions to be stored in an external memory unit 12 to establish a desired diagnostic assessment procedure. Execution of another module of the administration program by digital signal processing unit 42 allows the retrieval of diagnostic test data stored in external memory unit 12 when a diagnostic assessment procedure was conducted (i.e., when a patient or user executed a diagnostic procedure in accordance with the procedure).

The currently preferred embodiments of the invention utilize a microprocessor-based unit 10 that corresponds to the previously mentioned SUPER NINTENDO ENTERTAINMENT SYSTEM, with the invention being realized for diagnostic assessment of Attention Deficit Disorder and Attention Deficit Hyperactivity Disorder. In the current realization of the invention, program instructions for a battery of separate tests that assess various aspects of a juvenile's attention are stored in external memory unit 12. Two basic types of tests are employed: tests that include a series of delayed reaction tasks and tests that include a series of continuous performance tasks. In the delayed reaction tasks, programmable microprocessor-based unit 10 operates to generate an audible and/or visual warning signal to alert the user that the microprocessor-based unit soon will produce an audible and/or visual trigger stimulus. When the trigger stimulus is generated, the patient or user activates a designated switch or control of microprocessor-based unit 10 (e.g., a switch or control included in control switches 44 of FIG. 2). In current practice, the clinician or other administrator of the diagnostic assessment procedure can select one or more audio delayed reaction tests and/one or more video delayed reaction tests when establishing a battery of tests for a particular patient or user. As shall be described relative to FIGS. 6–11, the clinician establishes the battery of tests by executing a computer program, which also allows the clinician or administrator to establish the sequence in which various tests will be administered and, for each audio or visual delayed reaction test, select both the number of trigger stimuli to be generated and a time delay range. The time delay range establishes the upper and lower bounds of the delay between warning stimuli and trigger stimuli. The specific delay between a particular warning stimulus and its associated trigger stimulus is selected randomly by microprocessor-based unit 10 when the delayed reaction test is conducted.

Each time that microprocessor-based unit 10 generates a trigger stimulus, a timer (e.g., clock circuit 54 of FIG. 2) is activated. If the patient or user does not activate the appropriate switch or control within a predetermined time interval, a digital signal is stored indicating a failure to respond. On the other hand, if the patient or user responds, a digital signal is stored indicating the user's reaction time (i.e., the time period between the occurrence of a trigger stimulus and the patient's reaction). Since a series of delayed reaction tasks is used in each audio or visual delayed reaction test, the stored data that are accumulated during the diagnostic assessment will allow later analysis to determine various measures that relate to the patient's degree of attention. For example, measures that can be important include the user's fastest reaction time, his or her mean reaction time, and the standard deviation of reaction times. In addition, the difference between the results for audio and visual delayed reaction tasks may also be considered. For example, young children tend to respond more quickly to audio trigger stimuli than video trigger stimuli. Thus, the relationship between the results of audio and video delayed reaction tests for a patient may provide some insight as to that patient's relative deficit or development of both auditory and visual attention skills.

Figure 4:
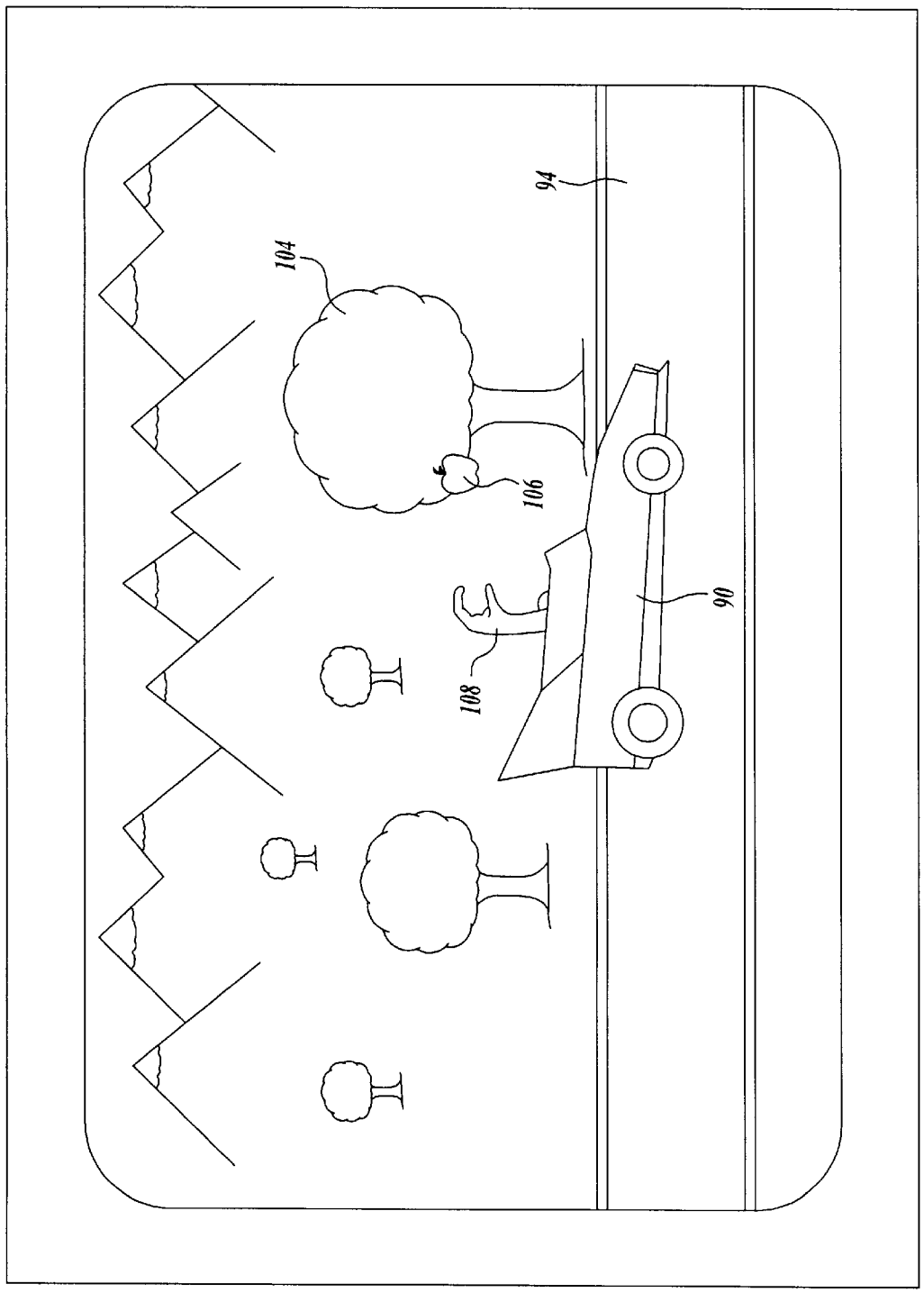
FIG. 4 illustrates a graphic display suitable for use when a microprocessor-based patient unit administers continuous performance tests in an embodiment of the invention that is configured and programmed for diagnostic measurement relating to Attention Deficit Hyperactivity Disorder and Attention Deficit Disorder.

In the currently preferred realizations of embodiments for use in diagnostic assessment of Attention Deficit Hyperactivity Disorder and Attention Deficit Disorder, external memory unit 12 is programmed to cause microprocessor unit 10 to generate a display of the type shown in simplified form in FIG. 4. In the display of FIG. 4, a car 90 is positioned at a starting line 92 on a roadway or racetrack 94. A traffic signal 96, having a red light 98, an amber light 100, and a green light 102, is prominently displayed. As each visual delayed reaction task is generated, microprocessor-based unit 10 causes sequential illumination of red light 98, amber light 100, and green light 102. Amber light 100 serves as the warning stimulus, with green light 102 providing a trigger stimulus after a randomly generated time delay that is within the time delay range that was established when the visual delayed reaction test being executed was established by the clinician or the administrator having control over the diagnostic testing.

Figure 3:
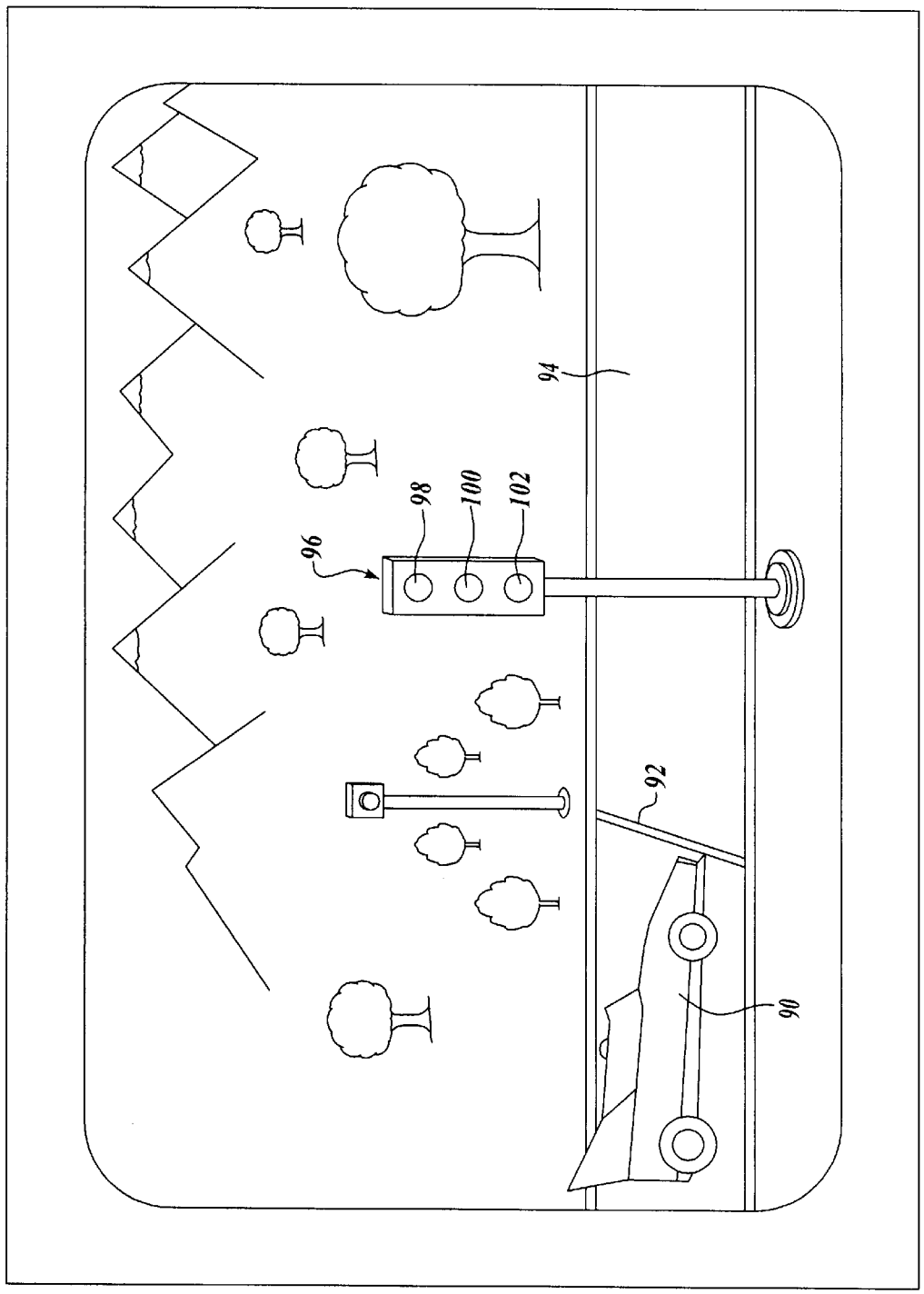
FIG. 3 illustrates a graphic display suitable for use when a microprocessor-based patient unit administers a delayed reaction tests in an embodiment of the invention that is configured for diagnostic measurements relating to Attention Deficit Hyperactivity Disorder or Attention Deficit Disorder.

During the audio delayed reaction tests, the three lights of traffic light 100 in FIG. 3 are extinguished and program instructions that are stored in external memory unit 12 result in generation of suitable audio warning and trigger stimuli by sound generator 62 of FIG. 2. In arrangements having sufficient memory and sound generation capability, the words "ready . . . set . . . go" are used, with the time interval between "set" and "go" being a random value within the range of values selected when a clinician established the diagnostic procedure. Two tones that are clearly distinct from one another also can be used for the warning and trigger stimuli.

The currently preferred realizations of embodiments of the invention that are directed to diagnostic assessment of Attention Deficit Hyperactivity Disorder and Attention Deficit Disorder provide for both visual and audible continuous performance tests. In each test a sequence or series of events occurs for which the patient or user is to respond by activating a predetermined switch or control such as the control switches 44 in the arrangement of FIG. 2. The continuous performance test used in the currently preferred embodiments of the invention are performance-paced in that the interstimulus stimulus interval (i.e., the time that elapses between consecutive stimuli) is reduced by a predetermined amount each time a correct response is made and is increased by the same or a different predetermined amount if an improper response occurs (i.e., the user responds to a non-target stimulus or fails to respond to a target stimulus).

The video display for the continuous performance tests of the currently preferred embodiments is indicated in FIG. 4. In FIG. 4, the car 90 that is used in the above-discussed delayed reaction tests is shown traveling along a roadway 94. Periodically, the car 90 approaches a tree 104, which is positioned along side roadway 94. As car 90 approaches a tree 104, various types of fruit (oranges, apples, lemons, and grapes) will appear, hanging downwardly from a branch of the tree. The object is for the patient or user to respond to a specified type of fruit only (e.g., apple 106 in FIG. 4) by depressing a selected switch such as one of the switches of control switches 44 in FIG. 2. When the appropriate switch is pressed, a hand and arm extend upwardly from car 90 to capture the fruit. As previously noted, with each correct response, the interstimulus interval is decreased (i.e., the car 90 appears to travel at a higher rate of speed) and with each incorrect response or failure to respond, the interstimulus interval is increased (car 90 appears to travel slower).

In the audio continuous performance tests of the referenced realizations of the invention, the display shows car 90 traveling at night, with only a portion of roadway 94 being illuminated by the car's headlights. Each time the car approaches a darkened tree 104, a low-frequency radar-like "beep" is heard if the tree does not bear the desired fruit (apple 106 in FIG. 4). When the proper fruit is present, a high-pitched radar-like beep is emitted.

Figure 5:
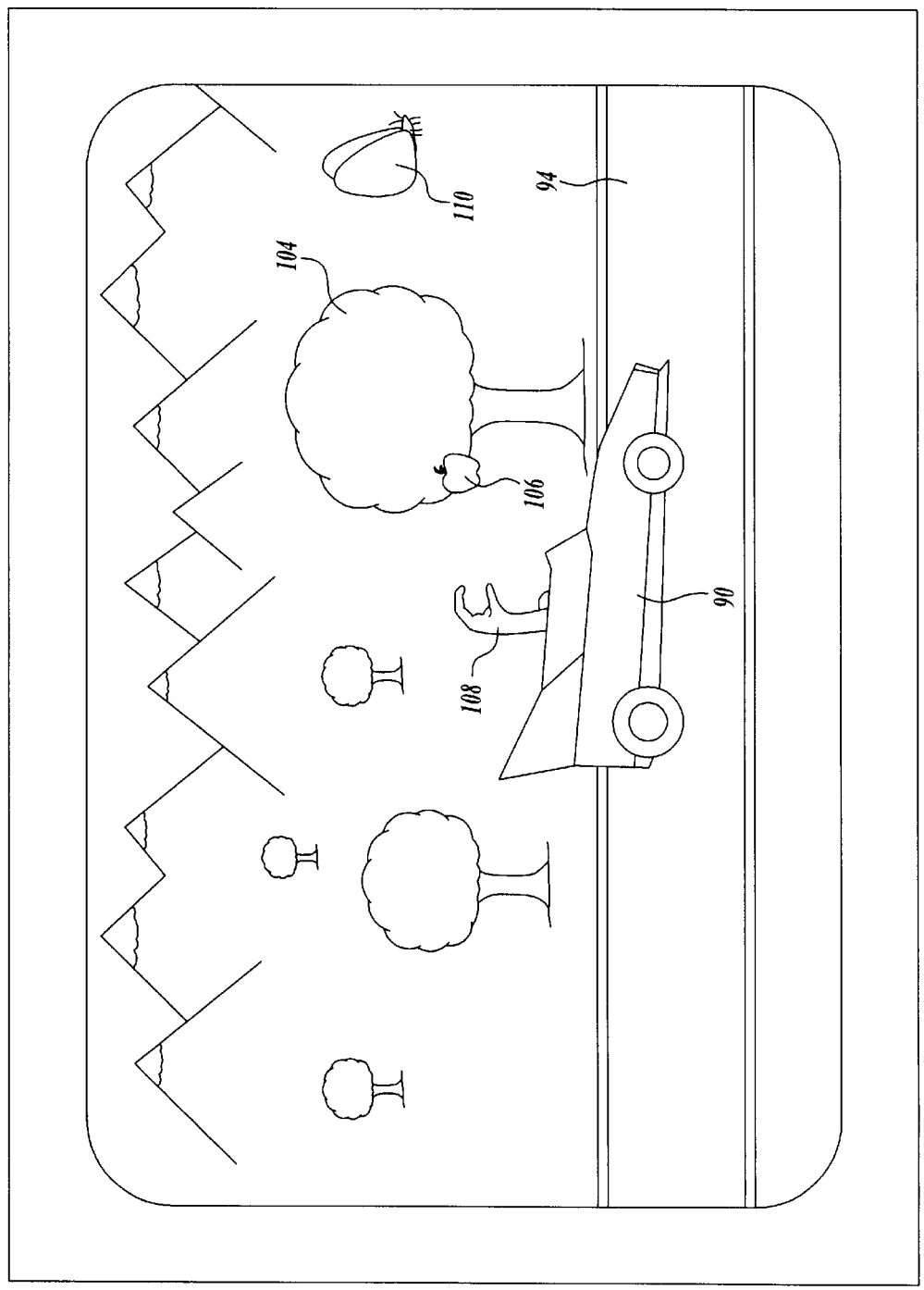
FIG. 5 illustrates a graphic display suitable for use when a microprocessor-based patient unit administers continuous performance tests that also include visual distractions in an embodiment of the invention that is configured and programmed for diagnostic measurement relative to Attention Deficit Hyperactivity Disorder and Attention Deficit Disorder.

Embodiments of the invention for diagnostic assessment for Attention Deficit Hyperactivity Disorder and Attention Deficit Disorder can also include programming for conduction of continuous performance tests that include distractions. For example, as is shown in FIG. 5, a fluttering butterfly 110 or other moving object such as a hopping frog or flying saucer can be generated in the peripheral region of the video display to provide a measure of the patient's degree of distractibility. During audio continuous performance tests synthesized voice signals such as "Now!" or "Go!" can be generated by microprocessor-based unit 10. In situations in which synthesized voice is beyond the capability of the sound generator being used, the microprocessor-based unit 10 can supply various distractive sounds or noises.

When the battery of diagnostic assessments is established by a clinician, program instructions can be stored in external memory unit 12 (or otherwise provided to a microprocessor-based unit) to determine the number of continuous performance tests to be performed and the type of each test (i.e., video without distractions; video with distractions; audio without distractions; and, audio with distractions). The sequence of the tests, both with respect to one another and with respect to the previously discussed delayed reaction tests, is also determined by the clinician. For each continuous performance test, the clinician can select the total number of target and non-target stimuli to be presented; the test duration; and the minimum stimulus duration (which is typically set at around 100 milliseconds). Diagnostic measures that are recorded in external memory unit 12 during conduction of continuous performance tests include: the number of target stimuli correctly identified (i.e., captured); the number of target stimuli for which the user failed to react (missed stimuli); the number of non-target stimuli for which there was a response; the number of times the button or switch was activated after a stimulus passed (late hits); and the final interstimulus interval (and/or the minimum interstimulus interval attained during the test).

As was described relative to FIGS. 1 and 2, program instructions for establishing the diagnostic assessment procedure (e.g., storing suitable program instructions in external memory 12) and retrieval of signals representative of the diagnostic measures gathered during diagnostic testing (e.g., accessing information stored in external memory 12) are performed by executing an administrator program with the clinician's computer (22 in FIG. 1; digital signal processing unit 42 in FIG. 2). When the administrator program of the current realizations of the invention is executed, a main menu screen is displayed, allowing the clinician to select menu items that include: the opening of a new file (i.e., establishing a diagnostic assessment procedure for a new patient or subject); opening an existing file; saving a file (storing a diagnostic assessment configuration in memory of the clinician's computer); closing a file; and producing the diagnostic assessment procedure (i.e., storing the appropriate program instructions in an external memory 12 or, alternatively, initiating execution of a diagnostic assessment procedure with a microprocessor-based unit 10 that is directly connected to the clinician's computer (FIG. 2).

Figure 6:
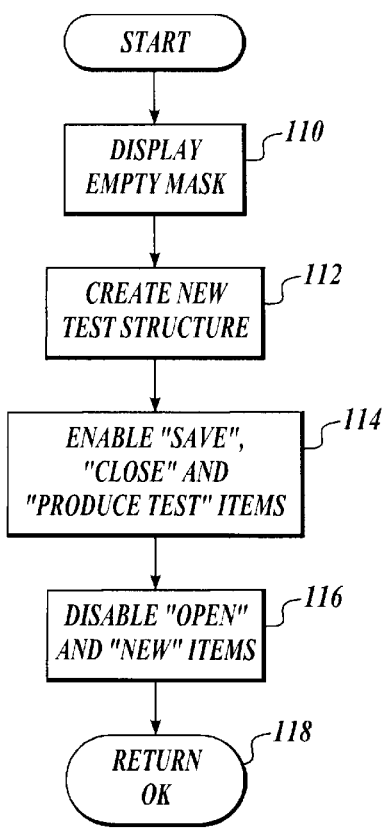
FIGS. 6–11 are sequence diagrams that illustrate operation of a clinician's computer during periods of time in which the computer is used to establish a battery of tests to be administered by the microprocessor-based unit; is used to supply program instructions to the microprocessor-based unit that will result in the desired psychological diagnostic testing; and, is used to retrieve diagnostic measurements obtained by the microprocessor-based unit during the administration of the diagnostic test.

The sequence of steps that is executed when a new file is opened during execution of the administrator program is shown in FIG. 6. As is indicated at block 110, the first step of opening a new file is the display of a "mask," i.e., a form that includes empty fields for insertion of information such as the name of the patient or subject, age, sex, grade or educational level, date on which the test is to be performed, name of attending physician or clinician; and the identity of the person establishing the diagnostic assessment procedure.

The next step of establishing a new file is indicated at block 112 and consists of creating the desired diagnostic assessment procedure. In this step, a set-up screen is displayed that allows the clinician or test administrator to establish a desired battery of the previously described audio and visual delayed reaction tests and the previously described audio and visual continued performance tests (both with and without distractions). The tests can be selected in any sequence and, if desired, a particular type of test can be repeated without intervening execution of a different type of test. Further, in the currently preferred realizations of the invention, a short training procedure is available for both delayed reaction testing and continuous performance testing. In most cases, the clinician or administrator will include one or both of the training procedures in the diagnostic assessment procedure.

The set-up screen also includes provision for the clinician or administrator to select the various previously mentioned delayed reaction test parameters and continuous performance test parameters. Specifically, the clinician can select the delay range that will determine the upper and lower limits of the random time delay between a warning stimulus and a trigger stimulus in the delayed reaction tests and can also set the number of trigger stimuli that will occur during each delayed reaction test. With respect to each continuous performance test, the set-up screen allows the clinician to set the duration of each test, the percentage of target stimuli (i.e., the mix of non-target and target stimuli), the amount by which the interstimulus interval decreases each time a patient or subject captures a target stimulus; the amount by which the interstimulus interval increases when the patient misses; and the type of target stimulus to be used (e.g., apples, grapes, lemons, or oranges).

Once the diagnostic assessment procedure has been established for a patient or subject, the sequence for establishing a new file causes the "save," "close," and "produce test" sequences of the administrator program to be enabled (indicated at block 114) and disables the "open" and "new" sequences of the administrator program. As is indicated at block 118 in FIG. 7, the sequence then returns to the menu screen. Since the "open" and "new" sequences have been disabled, those menu items are preferably at least partially blanked out or otherwise indicated as not being available for selection.

Figure 7:
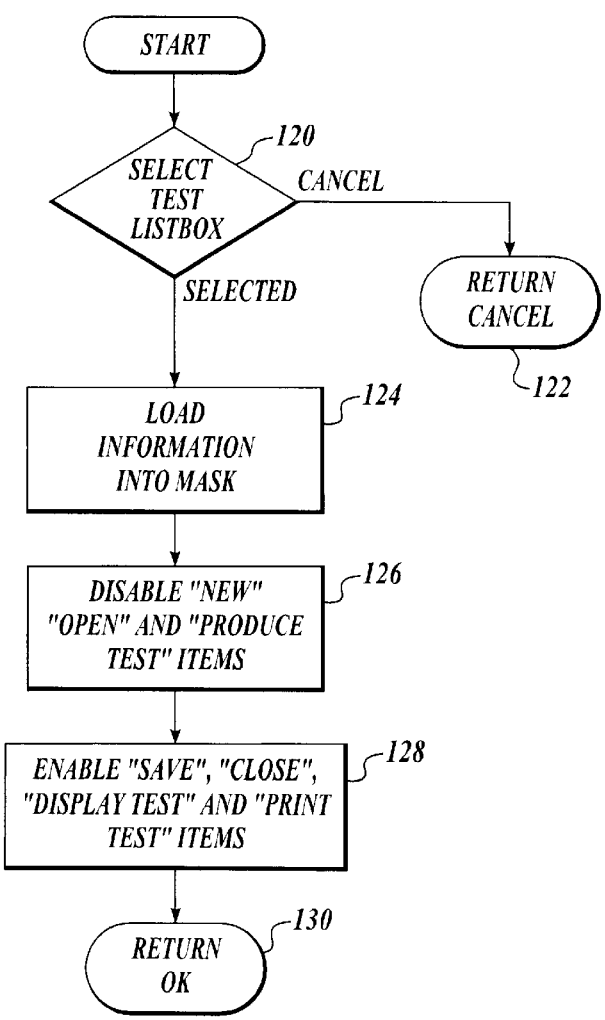

When the administrator program is initiated, the clinician can select the "open file" menu item as an alternative to the "new file" item. As is indicated in FIG. 7, the sequence that is executed when the "open file" menu item is selected begins with the display with a list of existing files (e.g., patient names or identification numbers), which is indicated at block 120. Also displayed is an option that allows the clinician or administrator to cancel the sequence for opening a file. If selected, the option for canceling the sequence returns the screen display to a display of the main menu (indicated at block 122). On the other hand, if the clinician or administrator selects a particular patient, the information about the patient and the battery of tests and test parameters that was recorded during the new file procedure is displayed (indicated at block 124). As is shown at block 126, the administrator program then sequences to disable menu items that would otherwise allow the opening of a new or different. The menu item that allows the production of a diagnostic test routine (such as the loading of an external memory unit 12 with program instructions) also is disabled. As is indicated at block 128, menu items for saving a file, closing a file, and for displaying or printing test results that were stored when the diagnostic assessment procedure for that patient was conducted or enabled.

The system then returns to displaying the menu with the enabled menu items being displayed in a manner that distinguishes those menu items from the disabled menu items (indicated at block 130).

Figure 8:
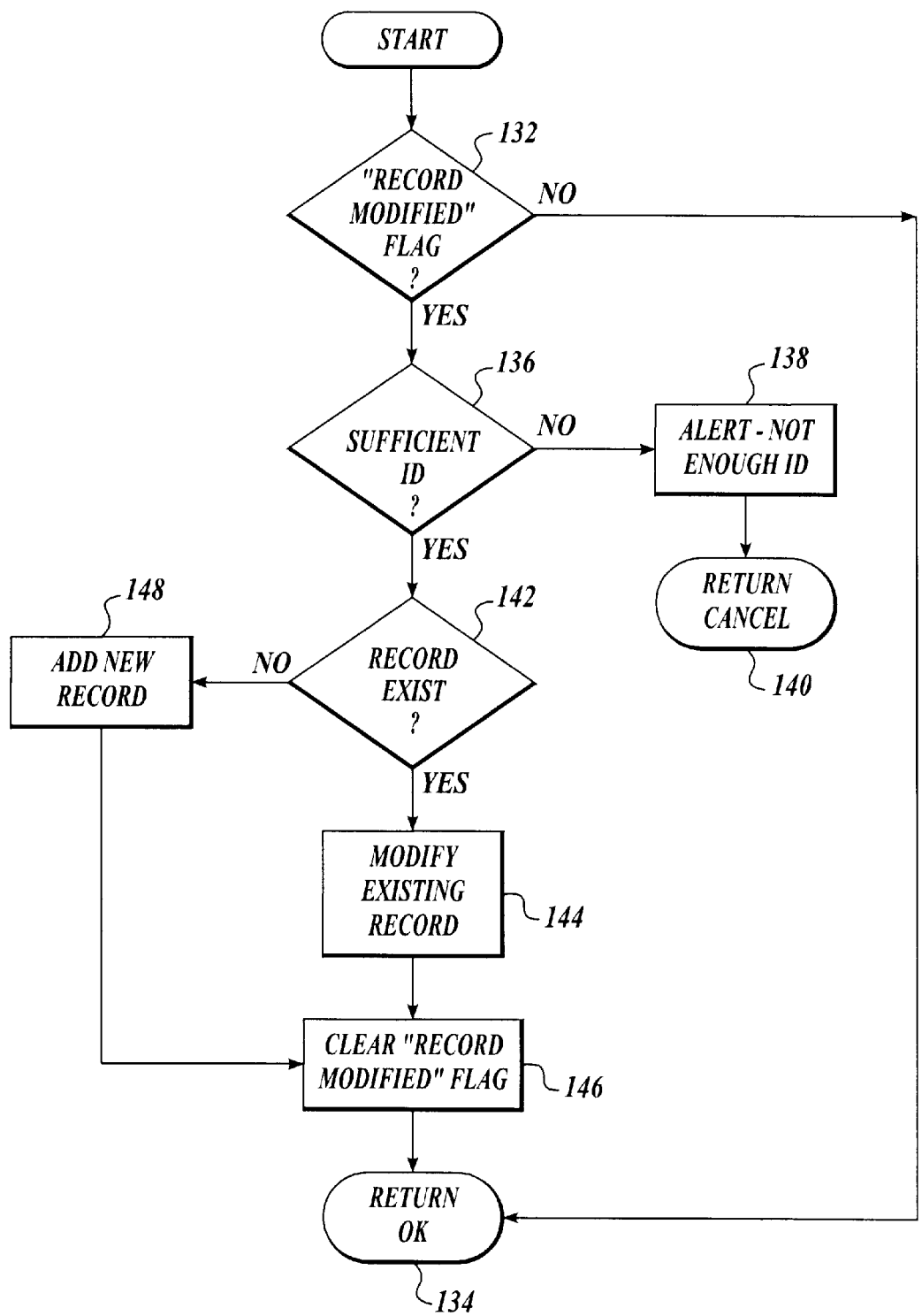

The sequence that is executed when the administrator program is used to save a patient file is shown in FIG. 8 and begins with a determination of whether a "record modified" is set (block 132). The record modified flag is a field in the data record for each patient and is set whenever that patients file is opened and modified by adding new information, or changing information that was previously entered. If the record modified flag is not set, the sequence shown in FIG. 8 is terminated and the system display returns to the selection menu (indicated at block 134). On the other hand, if the record modified flag is set, a determination is made as to whether sufficient patient identification information is included in the patient file or record being processed (indicated at decision block 136). In the event of insufficient identification a warning message is displayed (block 138). The sequence for saving the file is canceled and the display returns to the main menu (indicated at block 140).

When sufficient patient identification is included in the record being processed, the administrator program determines whether the record already exists (decision block 142). As is shown at block 144, an existing file is modified in accordance with information included in the file being saved. Next, the record modified flag is cleared (block 146); and the system display is returned to the main menu (block 134). However, if the file being processed does not already exist, a new record is stored in system memory (block 148); the record modified flag is cleared (block 146); and the system display is returned to the main menu (block 134).

Figure 9:
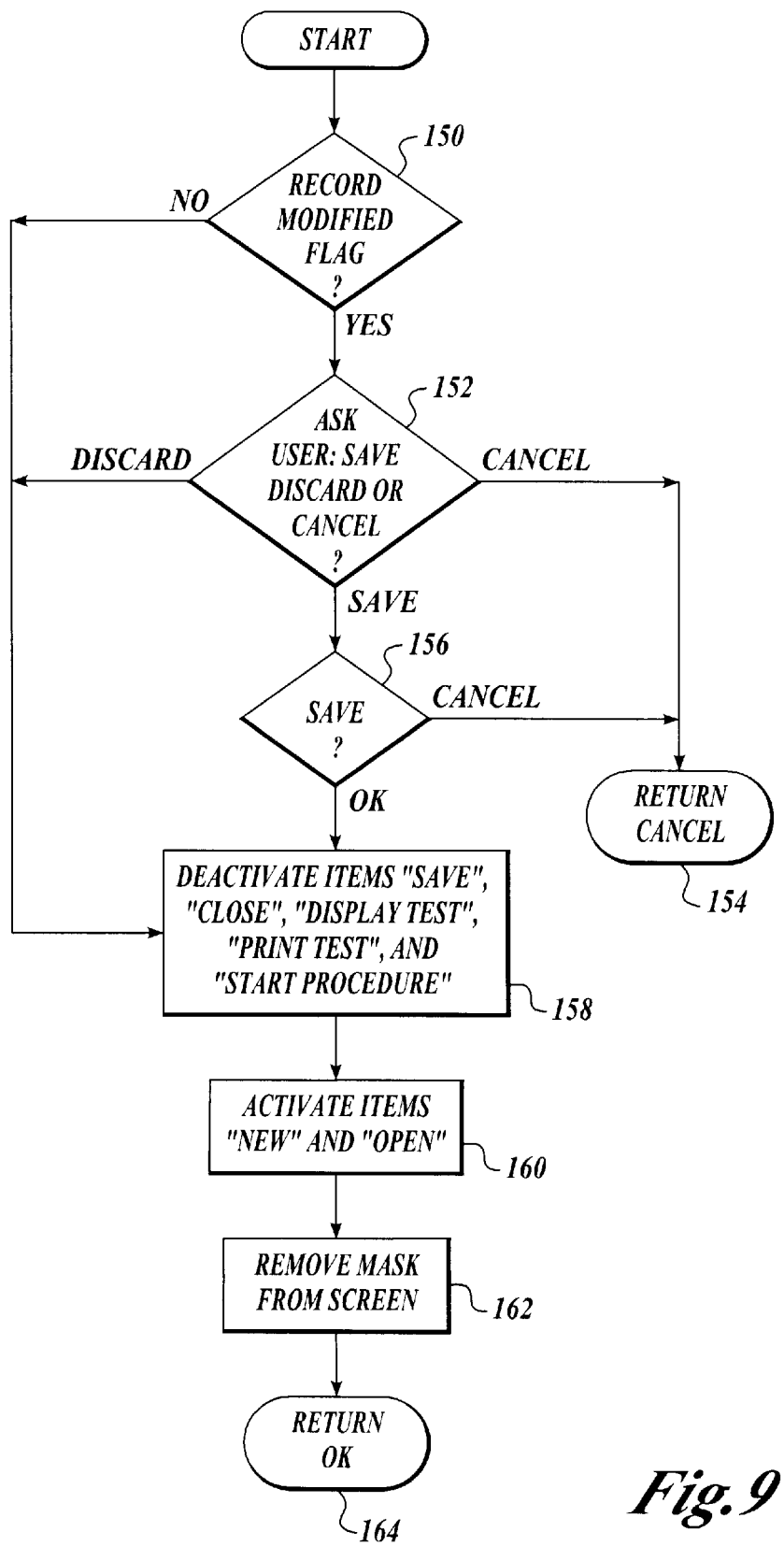

As is shown in FIG. 9, the sequence by which the administrator program closes a previously opened patient record begins with a determination of whether the record modifier flag is set (indicated at decision block 150). If the record has been modified, the clinician or administrator executing the program is prompted to specify whether the modified record should be saved, discarded, or whether the sequence to close the record should be canceled (indicated at block 152). As is indicated at block 156, if the modified record is to be saved, the above-discussed sequence for saving the record is executed.

A determination at decision block 150 that the record has not been modified causes deactivation of the menu items for saving a file or record, closing a file, and for displaying and printing test results. The menu item that allows storage of program instructions in an external memory 12 or the alternative administration of a diagnostic assessment procedure with a microprocessor-based unit 10 that is connected to the clinician's computer is also disabled (all indicated at block 158 in FIG. 9). As is shown in FIG. 9, these menu items also are disabled after saving a modified file (i.e., the completion of the operation indicated at block 156) and, in addition, upon executing an instruction to discard a modified record (shown at block 152). As is indicated at block 160, once the specified menu items have been disabled, the menu items for establishing a new file and for opening an existing file are enabled (block 160); the record is removed from the display screen (block 162); and the main menu is displayed (block 164).

Figure 10:
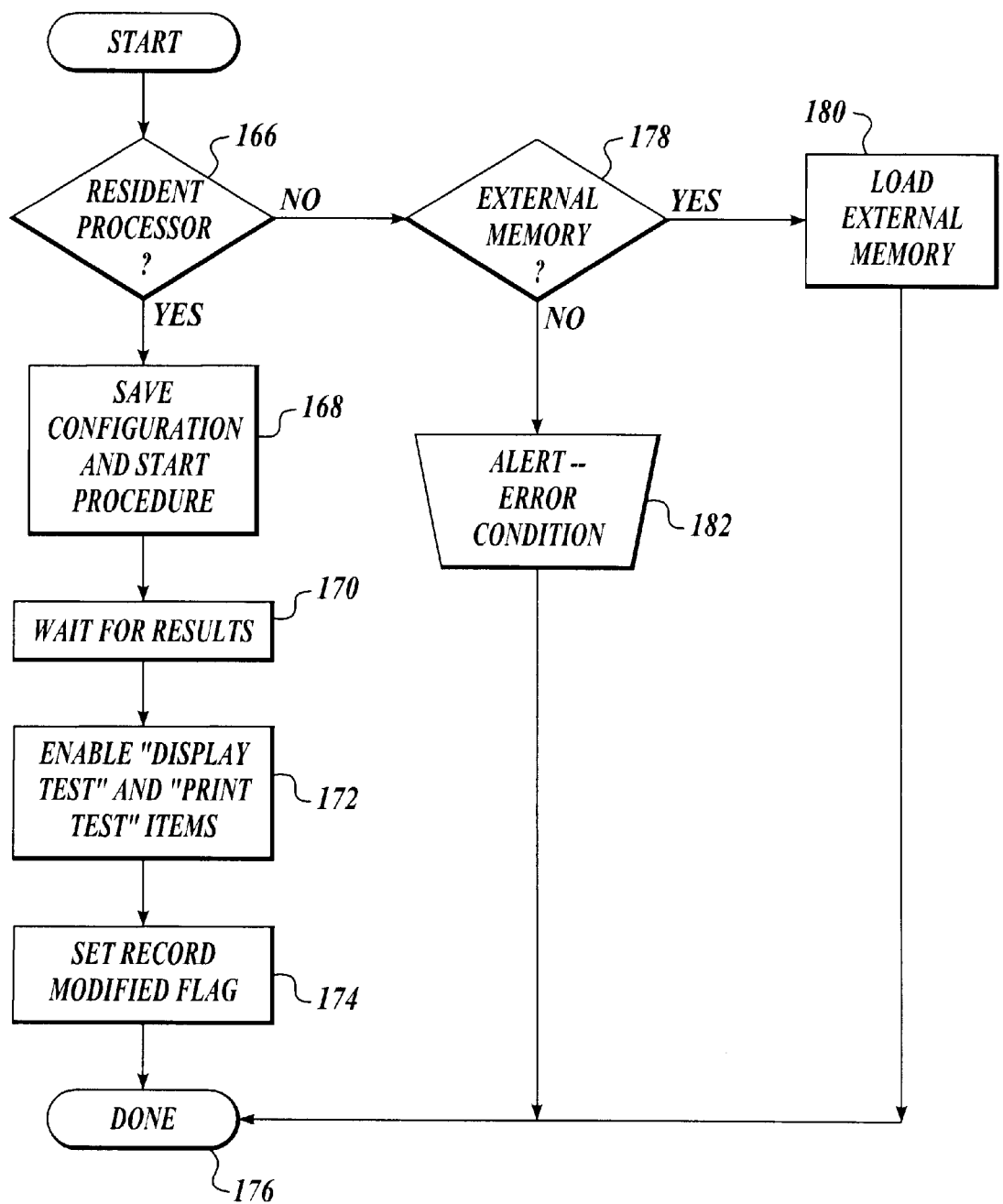

The sequence that is executed during the administrator program to load desired program instructions into an external memory unit 12 or, alternatively, initiate a diagnostic assessment procedure with a microprocessor-based unit 10 that is electrically connected to the clinician's computer is shown in FIG. 10. As is indicated at decision block 166, the sequence begins with a determination of whether a microprocessor-based unit 10 is both connected to the clinician's computer and is turned on. If a microprocessor-based unit is both connected and active, the program instructions required to configure the microprocessor for the test specified in the currently open patient file are transferred to the microprocessor-based unit (block 168). The sequence then remains in a "wait" state until the microprocessor 10 signals that the diagnostic test results are available (block 170). Once the test results are available and stored in memory, the menu items for displaying test results and printing test results are enabled (block 172); the previously discussed record modified flag is set (block 174); and the system display returns to the main menu (block 176).

When a microprocessor unit 10 that is electrically connected with the clinician's computer is not turned on (determined at block 166), a determination is made at block 178 as to whether an external memory unit 12 is to be loaded with program instructions (e.g., whether an external memory unit 12 is present in receptacle 38 of the arrangements shown in FIGS. 1 and 2). If an external memory unit 12 is not present, a message is displayed indicating that an error condition has been encountered (block 182) and the administrator program sequences to the main menu screen (block 176). If an external memory unit 12 is present, the program instructions for establishing a diagnostic assessment procedure for the open patient file are loaded into the external memory unit 12 for subsequent use by the patient.

Figure 11:
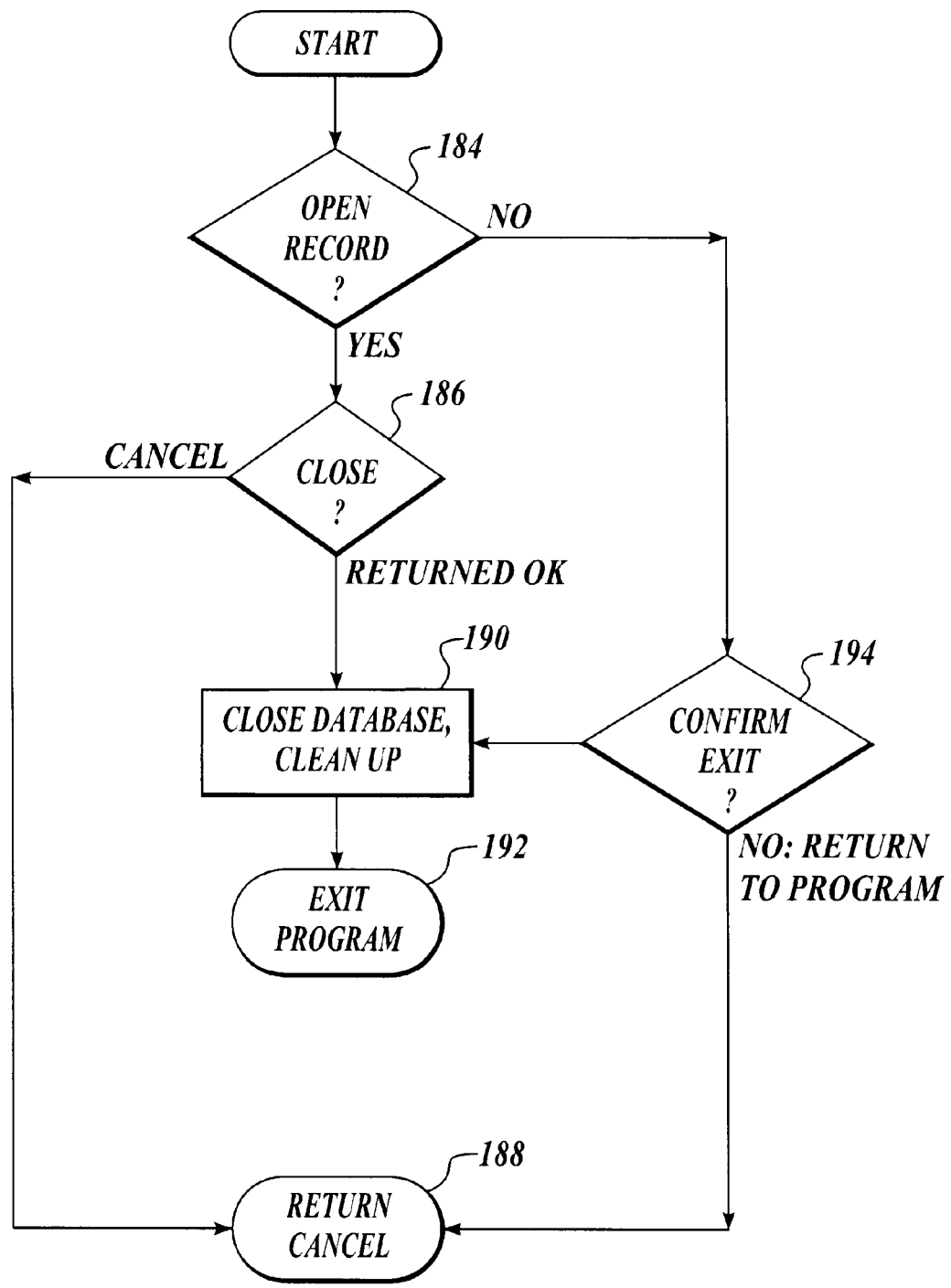

Referring to FIG. 11, the sequence by which the clinician or administrator exits the administrator program begins with the determination as to whether a patient file or record is open (decision block 184). If an open patient file or record is detected, the sequence for closing the file that was discussed relative to FIG. 9 is executed (indicated at block 186). If the sequence for closing the file is canceled prior to completion, the sequence for exiting the administrator program is canceled and the main menu is displayed (indicated at block 188). Successful completion of the sequence for closing an open file results in execution of "housekeeping" routines that close the database that stores test results and, in addition, perform memory cleanup operations (indicated at block 190); and the administrator program is removed from active memory (indicated at block 192).

If no record is open when the exit sequence is executed (determined at block 184), the clinician is prompted to confirm whether an exit from the administrator program is to be made (indicated at block 194). If the exit command is verified, the database of test results is closed and memory cleanup accomplished (block 190), with subsequent exit from the administrator program (block 192). In the event exit is not to be made, the main menu is again displayed (block 188).

While the preferred embodiment of the invention has been illustrated and described, it will be appreciated that various changes can be made therein without departing from the spirit and scope of the invention. As previously mentioned, the invention can be embodied in various ways to provide a microprocessor-based unit with program instructions that cause the microprocessor-based unit to operate in a manner suitable for the assessment of various psychological conditions. For example, in assessing and treating habitual smoking or addiction to nicotine, a microprocessor-based unit (e.g., video game system) can be programmed to present a game-like presentation that may or may not directly relate to smoking. Such a unit can be given to a user with instructions to "play" the game-like presentation each time the user has an urge to smoke over a predetermined period such as three weeks. At the end of the prescribed period, the clinician can access the stored information and based on computer assisted analysis of the retrieved data can determine the nature, frequency and severity of the user's habit or addiction, as well as the motivation or stimulus that triggers an urge to smoke. Based on that information, an informed decision can be reached as to whether the user of the system (e.g., patient) is likely to respond to behavioral therapy or whether chemical replacement therapy or a combination of the two therapies should be used. Various other addictions and behavioral patterns can be assessed in similar fashion.

As another example of the manner in which the invention can be embodied, a series of interactive assessment sessions for conditions such as depression or anxiety can be presented via interactive cable television to a wide audience. In such an arrangement, the patient or subject is enrolled in the sessions by a psychiatrist or other healthcare professional. The patient or user tunes the interactive television system to a predetermined channel at a predetermined time and enters a personal identification code via a microprocessor-based unit that is connected for receiving and sending signals via the interactive television system. Program instructions are then provided to the microprocessor-based unit via the interactive television system and the patient or user responds to various stimuli during the televised diagnostic assessment section. As is the case with other arrangements of the invention, the televised assessment session can be in a game-like format or other presentation that is unobtrusive. Diagnostic information gathered during the session can be provided to the clinician in one of the several ways discussed with respect to FIGS. 1 and 2. By analyzing the diagnostic assessment data gathered during the interactive assessment sessions, the psychiatrist or other healthcare professional can make a better informed decision as to the need for clinical therapy and/or medication than can be made based only on traditional clinical sessions.

The invention further presents a system and method for remotely monitoring individuals and for communicating information to the individuals. In a preferred embodiment of the invention, the individuals are patients and the system is used to collect data relating to the health status of the patients. However, it is to be understood that the invention is not limited to remote patient monitoring. The system and method of the invention may be used for any type of remote monitoring application. The invention may also be implemented as an automated messaging system for communicating information to individuals, as will be discussed in an alternative embodiment below.

Figure 201:
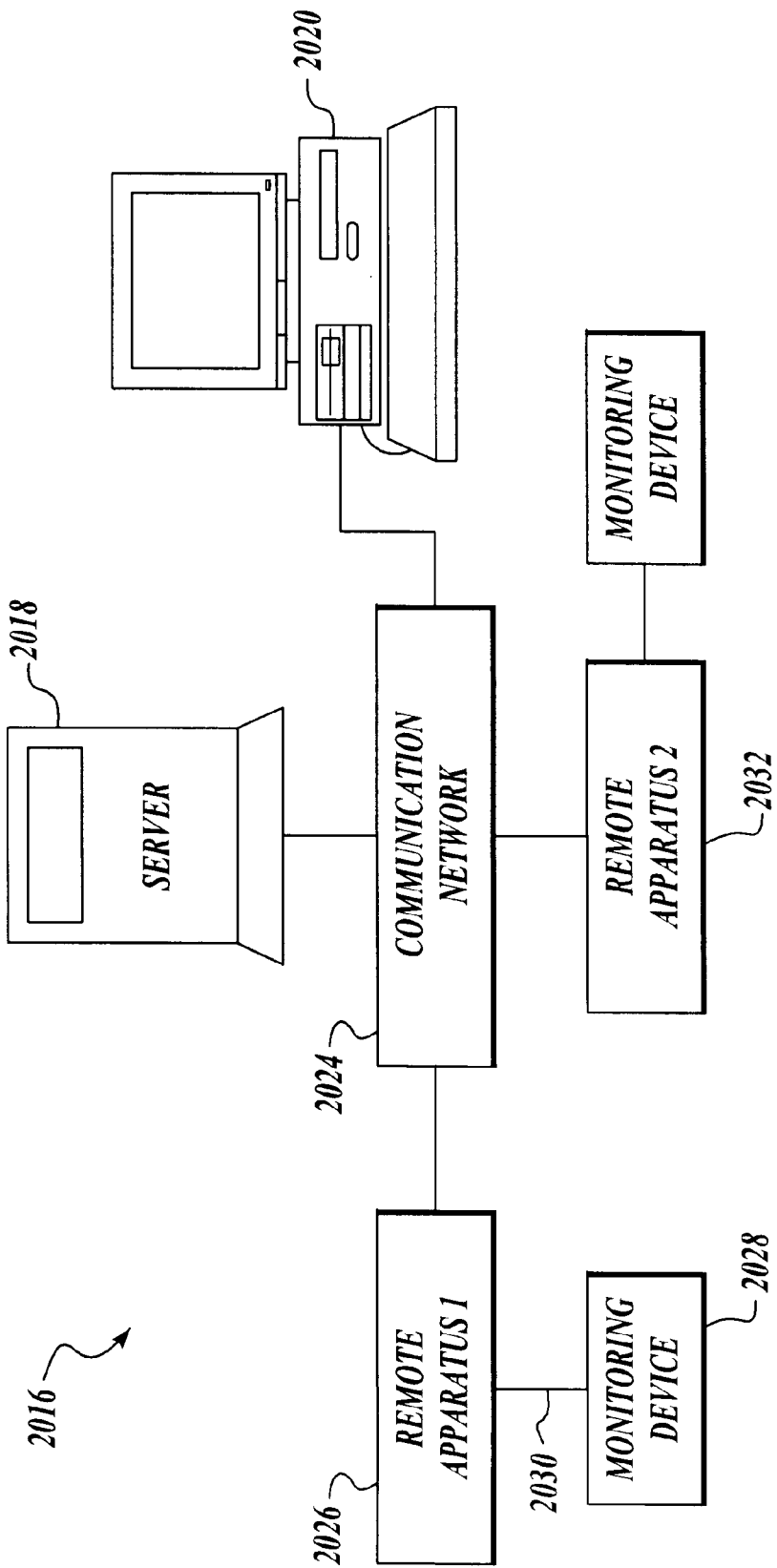
FIG. 201 is a block diagram of a networked system according to a preferred embodiment of the invention.

A preferred embodiment of the invention is illustrated in FIGS. 201–212. Referring to FIG. 201, a networked system 2016 includes a server 2018 and a workstation 2020 connected to server 2018 through a communication network 2024. Server 2018 is preferably a world wide web server and communication network 2024 is preferably the Internet. It will be apparent to one skilled in the art that server 2018 may comprise a single stand-alone computer or multiple computers distributed throughout a network. Workstation 2020 is preferably a personal computer, remote terminal, or web TV unit connected to server 2018 via the Internet. Workstation 2020 functions as a remote interface for entering in server 2018 messages and queries to be communicated to the patients.

System 2016 also includes first and second remotely programmable apparatuses 2026 and 2032 for monitoring first and second patients, respectively. Each apparatus is designed to interact with a patient in accordance with script programs received from server 2018. Each apparatus is in communication with server 2018 through communication network 2024, preferably the Internet. Alternatively, each apparatus may be placed in communication with server 2018 via wireless communication networks, cellular networks, telephone networks, or any other network which allows each apparatus to exchange data with server 2018. For clarity of illustration, only two apparatuses are shown in FIG. 201. It is to be understood that system 2016 may include any number of apparatuses for monitoring any number of patients.

In the preferred embodiment, each patient to be monitored is also provided with a monitoring device 2028. Monitoring device 2028 is designed to produce measurements of a physiological condition of the patient, record the measurements, and transmit the measurements to the patient's apparatus through a standard connection cable 2030. Examples of suitable monitoring devices include blood glucose meters, respiratory flow meters, blood pressure cuffs, electronic weight scales, and pulse rate monitors. Such monitoring devices are well known in the art. The specific type of monitoring device provided to each patient is dependent upon the patient's disease. For example, diabetes patients are provided with a blood glucose meters for measuring blood glucose concentrations, asthma patients are provided with respiratory flow meters for measuring peak flow rates, obesity patients are provided with weight scales, etc.

Figure 202:
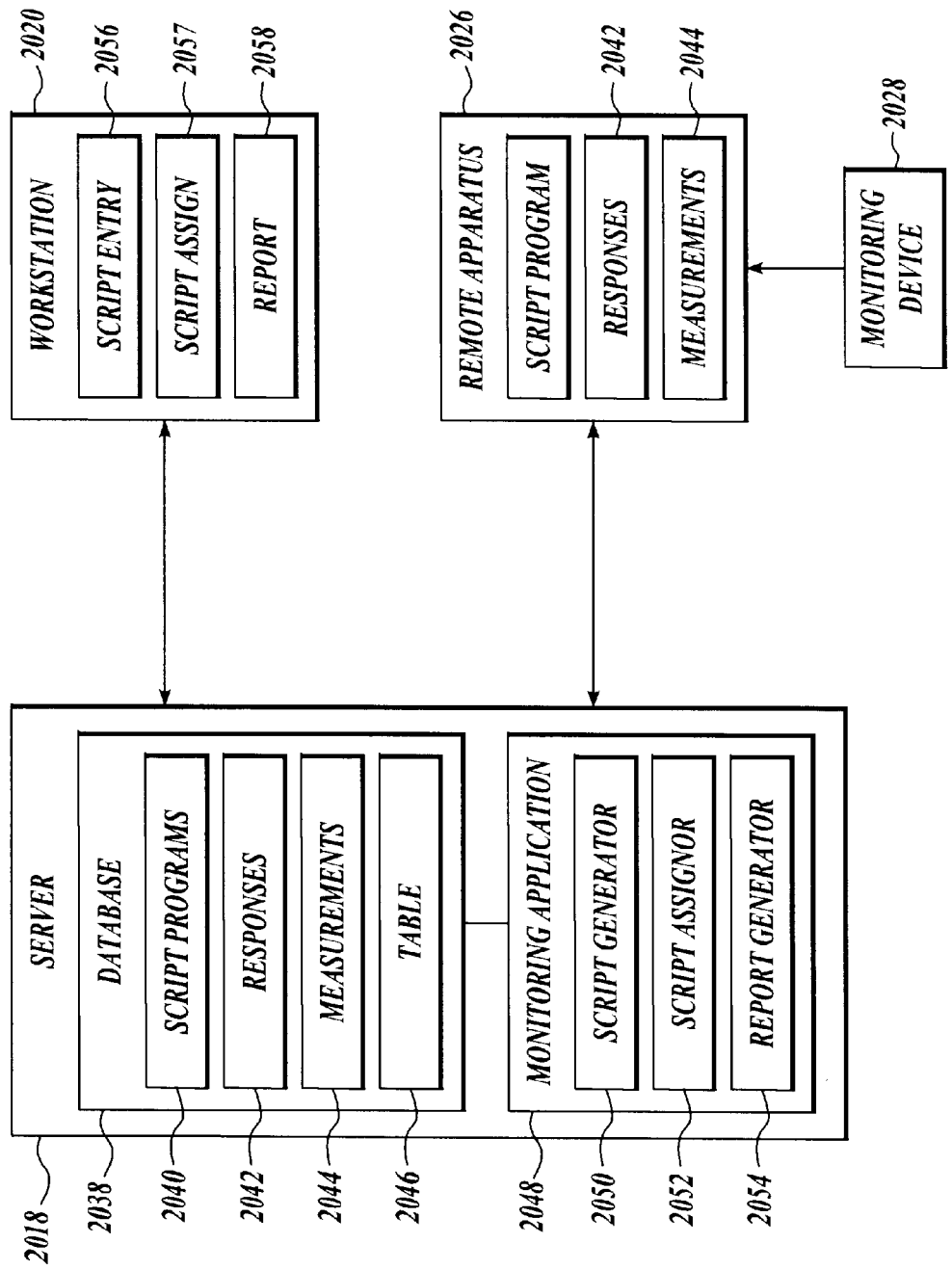
FIG. 202 is a block diagram illustrating the interaction of the components of the system of FIG. 201.

FIG. 202 shows server 2018, workstation 2020, and apparatus 2026 in greater detail. Server 2018 includes a database 2038 for storing script programs 2040. The script programs are executed by each apparatus to communicate queries and messages to a patient, receive responses 2042 to the queries, collect monitoring device measurements 2044, and transmit responses 2042 and measurements 2044 to server 2018. Database 2038 is designed to store the responses 2042 and measurements 2044. Database 2038 further includes a look-up table 2046. Table 2046 contains a list of the patients to be monitored, and for each patient, a unique patient identification code and a respective pointer to the script program assigned to the patient. Each remote apparatus is designed to execute assigned script programs which it receives from server 2018.

Figure 203:
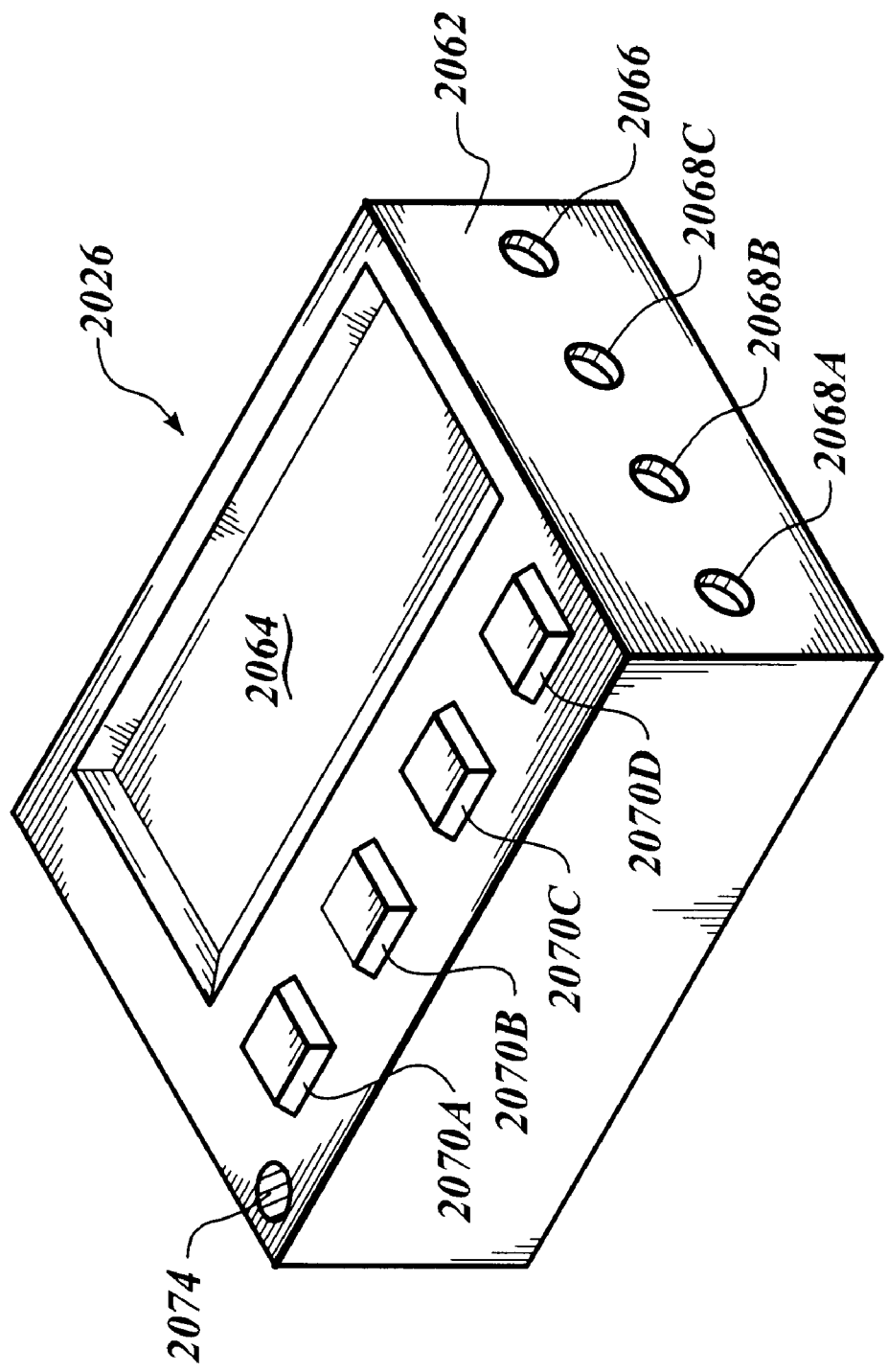
FIG. 203 is a perspective view of a remotely programmable apparatus of the system of FIG. 201.
Figure 204:
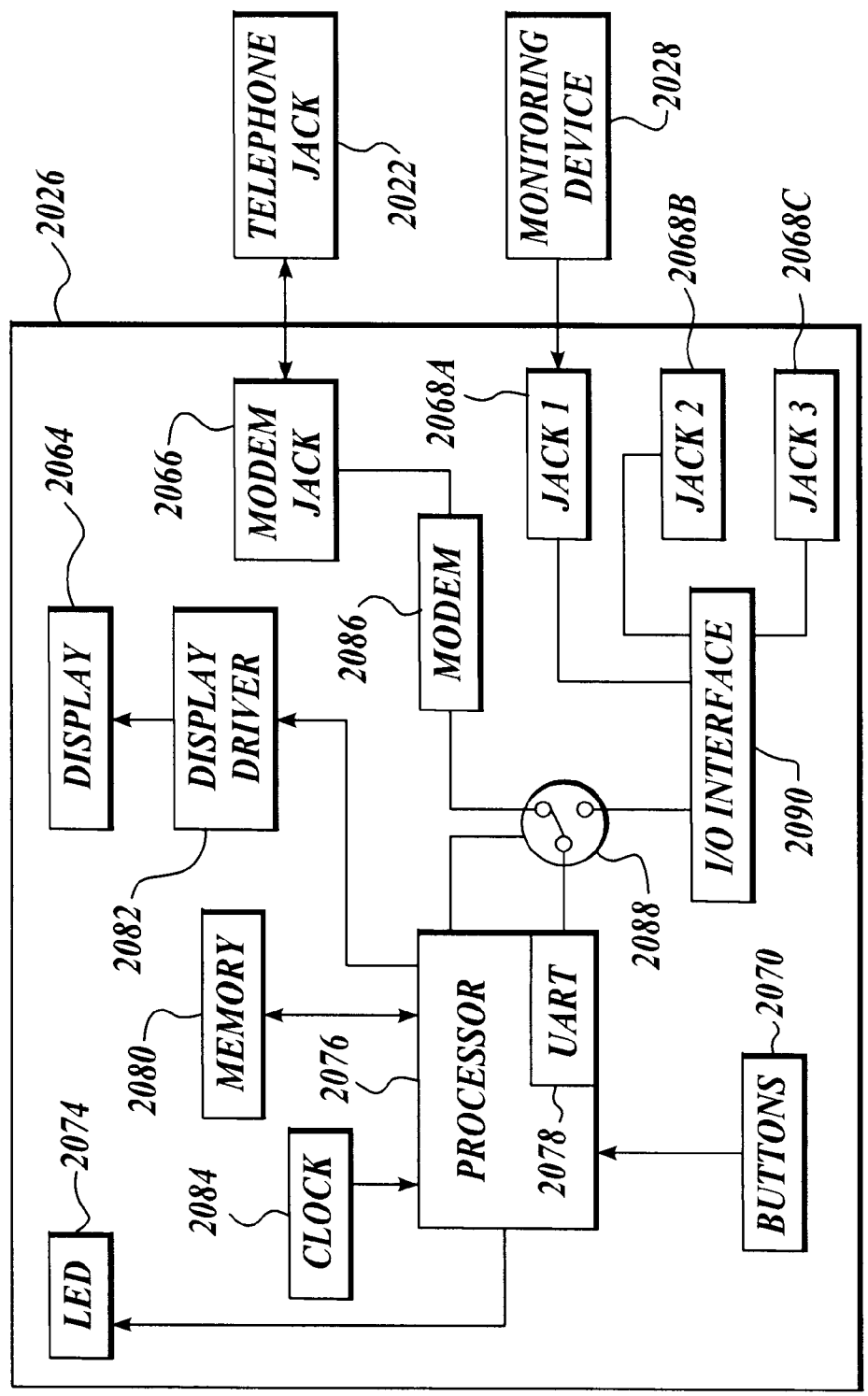
FIG. 204 is a block diagram illustrating the components of the apparatus of FIG. 203.

FIGS. 203–204 show the structure of each apparatus according to the preferred embodiment. For clarity, only apparatus 2026 is shown since each apparatus of the preferred embodiment has substantially identical structure to apparatus 2026. Referring to FIG. 203, apparatus 2026 includes a housing 2062. Housing 2062 is sufficiently compact to enable apparatus 2026 to be hand-held and carried by a patient. Apparatus 2026 also includes a display 2064 for displaying queries and prompts to the patient. In the preferred embodiment, display 2064 is a liquid crystal display (LCD).

Four user input buttons 2070A, 2070B, 2070C, and 2070D are located adjacent display 2064. The user input buttons are for entering in apparatus 2026 responses to the queries and prompts. In the preferred embodiment, the user input buttons are momentary contact push buttons. In alternative embodiments, the user input buttons may be replaced by switches, keys, a touch sensitive display screen, or any other data input device.

Three monitoring device jacks 2068A, 2068B, and 2068C are located on a surface of housing 2062. The device jacks are for connecting apparatus 2026 to a number of monitoring devices, such as blood glucose meters, respiratory flow meters, or blood pressure cuffs, through respective connection cables (not shown). Apparatus 2026 also includes a modem jack 2066 for connecting apparatus 2026 to a telephone jack through a standard connection cord (not shown). Apparatus 2026 further includes a visual indicator, such as a light emitting diode (LED) 2074. LED 2074 is for visually notifying the patient that he or she has unanswered queries stored in apparatus 2026.

FIG. 204 is a schematic block diagram illustrating the components of apparatus 2026 in greater detail. Apparatus 2026 includes a microprocessor 2076 and a memory 2080 connected to microprocessor 2076. Memory 2080 is preferably a non-volatile memory, such as a serial EEPROM. Memory 2080 stores script programs received from the server, measurements received from monitoring device 2028, responses to queries, and the patient's unique identification code. Microprocessor 2076 also includes built-in read only memory (TOM) which stores firmware for controlling the operation of apparatus 2026. The firmware includes a script interpreter used by microprocessor 2076 to execute the script programs. The script interpreter interprets script commands which are executed by microprocessor 2076. Specific techniques for interpreting and executing script commands in this manner are well known in the art.

Microprocessor 2076 is preferably connected to memory 2080 using a standard two-wire $I^2C$ interface. Microprocessor 2076 is also connected to user input buttons 2070, LED 2074, a clock 2084, and a display driver 2082. Clock 2084 indicates the current date and time to microprocessor 2076. For clarity of illustration, clock 2084 is shown as a separate component, but is preferably built into microprocessor 2076. Display driver 2082 operates under the control of microprocessor 2076 to display information on display 2064. Microprocessor 2076 is preferably a PIC 16C65 processor which includes a universal asynchronous receiver transmitter (UART) 2078. UART 2078 is for communicating with a modem 2086 and a device interface 2090. A CMOS switch 2088 under the control of microprocessor 2076 alternately connects modem 2086 and interface 2090 to UART 2078.

Modem 2086 is connected to a telephone jack 2022 through modem jack 2066. Modem 2086 is for exchanging data with server 2018 through communication network 2024. The data includes script programs which are received from the server as well as responses to queries, device measurements, script identification codes, and the patient's unique identification code which modem 2086 transmits to the server. Modem 2086 is preferably a complete 28.8 K modem commercially available from Cermetek, although any suitable modem may be used.

Device interface 2090 is connected to device jacks 2068A, 2068B, and 2068C. Device interface 2090 is for interfacing with a number of monitoring devices, such as blood glucose meters, respiratory flow meters, blood pressure cuffs, weight scales, or pulse rate monitors, through the device jacks. Device interface 2090 operates under the control of microprocessor 2076 to collect measurements from the monitoring devices and to output the measurements to microprocessor 2076 for storage in memory 2080. In the preferred embodiment, interface 2090 is a standard RS232 interface. For simplicity of illustration, only one device interface is shown in FIG. 204. However, in alternative embodiments, apparatus 2026 may include multiple device interfaces to accommodate monitoring devices which have different connection standards.

Referring again to FIG. 202, server 2018 includes a monitoring application 2048. Monitoring application 2048 is a controlling software application executed by server 2018 to perform the various functions described below. Application 2048 includes a script generator 2050, a script assignor 2052, and a report generator 2054. Script generator 2050 is designed to generate script programs 2040 from script information entered through workstation 2020. The script information is entered through a script entry screen 2056. In the preferred embodiment, script entry screen 2056 is implemented as a web page on server 2018. Workstation 2020 includes a web browser for accessing the web page to enter the script information.

FIG. 205 illustrates script entry screen 2056 as it appears on workstation 2020. Screen 2056 includes a script name field 2092 for specifying the name of a script program to be generated. Screen 2056 also includes entry fields 2094 for entering a set of queries to be answered by a patient. Each entry field 2094 has corresponding response choice fields 2096 for entering response choices for the query. Screen 2056 further includes check boxes 2098 for selecting a desired monitoring device from which to collect measurements, such as a blood glucose meter, respiratory flow meter, or blood pressure cuff.

Screen 2056 additionally includes a connection time field 2100 for specifying a prescribed connection time at which each apparatus executing the script is to establish a subsequent communication link to the server. The connection time is preferably selected to be the time at which communication rates are the lowest, such as 3:00 AM. Screen 2056 also includes a CREATE SCRIPT button 2102 for instructing the script generator to generate a script program from the information entered in screen 2056. Screen 2056 further includes a CANCEL button 2104 for canceling the information entered in screen 2056.

In the preferred embodiment, each script program created by the script generator conforms to the standard file format used on UNIX systems. In the standard file format, each command is listed in the upper case and followed by a colon. Every line in the script program is terminated by a linefeed character {LF}, and only one command is placed on each line. The last character in the script program is a UNIX end of file character {EOF}. Table 1 shows an exemplary listing of script commands used in the preferred embodiment of the invention.

| Command | Description |
| --- | --- |
| CLS: {LF} | Clear the display. |
| ZAP: {LF} | Erase from memory the last set of query responses recorded. |
| LED: b{LF} | Turn the LED on or off, where b is a binary digit of 0 or 1. An argument of 1 turns on the LED, and an argument of 0 turns off the LED. |
| DISPLAY: {chars}{LF} | Display the text following the DISPLAY command. |
| INPUT: mmmm{LF} | Record a button press. The m's represent a button mask pattern for each of the four input buttons. Each m contains an "X" for disallowed buttons or an "O" for allowed buttons. For example, INPUT: OXOX{LF} allows the user to press either button #1 or #3. |
| WAIT: {LF} | Wait for any one button to be pressed, then continue executing the script program. |
| COLLECT: device{LF} | Collect measurements from the monitoring device specified in the COLLECT command. The user is preferably prompted to connect the specified monitoring device to the apparatus and press a button to continue. |
| NUMBER: aaaa{LF} | Assign a script identification code to the script program. The script identification code from the most recently executed NUMBER statement is subsequently transmitted |

-continued

| Command | Description |
| --- | --- |
| | to the server along with the query responses and device measurements. The script identification code identifies to the server which script program was most recently executed by the remote apparatus. |
| DELAY: t{LF} | Wait until time t specified in the DELAY command, usually the prescribed connection time. |
| CONNECT: {LF} | Perform a connection routine to establish a communication link to the server, tramsmit the patient identification code, query responses, device measurements, and script identification code to the server, and receive and store a new script program. When the server instructs the apparatus to disconnect, the script interpreter is restarted, allowing the new script program to execute. |

The script commands illustrated in Table 1 are representative of the preferred embodiment and are not intended to limit the scope of the invention. After consideration of the ensuing description, it will be apparent to one skilled in the art many other suitable scripting languages and sets of script commands may be used to implement the invention.

Script generator 2050 preferably stores a script program template which it uses to create each script program. To generate a script program, script generator 2050 inserts into the template the script information entered in screen 2056. For example, FIGS. 206A–206B illustrate a sample script program created by script generator 2050 from the script information shown in FIG. 205.

The script program includes display commands to display the queries and response choices entered in fields 2094 and 2096, respectively. The script program also includes input commands to receive responses to the queries. The script program further includes a collect command to collect device measurements from the monitoring device specified in check boxes 2098. The script program also includes commands to establish a subsequent communication link to the server at the connection time specified in field 2100. The steps included in the script program are also shown in the flow chart of FIGS. 212A–212B and will be discussed in the operation section below.

Referring again to FIG. 202, script assignor 2052 is for assigning script programs 2040 to the patients. Script programs 2040 are assigned in accordance with script assignment information entered through workstation 2020. The script assignment information is entered through a script assignment screen 2057, which is preferably implemented as a web page on server 2018.

Figure 207:
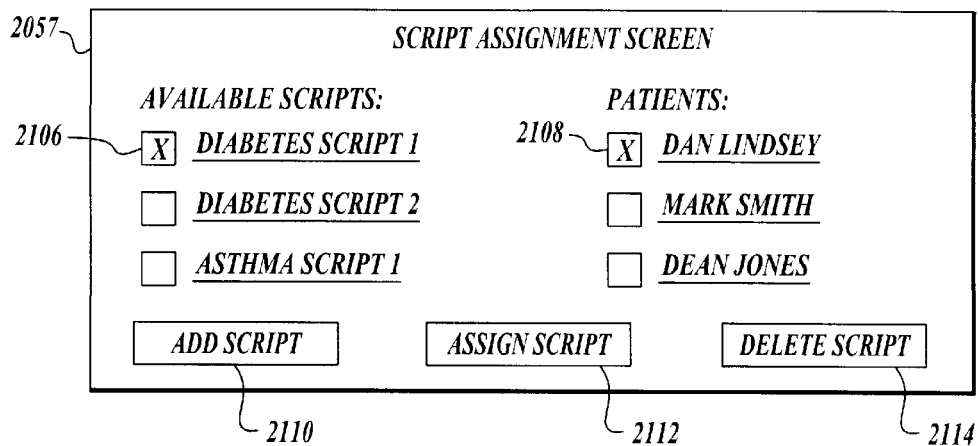
FIG. 207 is a script assignment screen according to the preferred embodiment of the invention.

FIG. 207 illustrates a sample script assignment screen 2057 as it appears on workstation 2020. Screen 2057 includes check boxes 2106 for selecting a script program to be assigned and check boxes 2108 for selecting the patients to whom the script program is to be assigned. Screen 2057 also includes an ASSIGN SCRIPT button 2112 for entering the assignments. When button 2112 is pressed, the script assignor creates and stores for each patient selected in check boxes 2108 a respective pointer to the script program selected in check boxes 2106. Each pointer is stored in the patient look-up table of the database. Screen 2057 further includes an ADD SCRIPT button 2110 for accessing the script entry screen and a DELETE SCRIPT button 2114 for deleting a script program.

Referring again to FIG. 202, report generator 2054 is designed to generate a patient report 2058 from the responses and device measurements received in server 2018. Patient report 2058 is displayed on workstation 2020. FIG. 210 shows a sample patient report 2058 produced by report generator 2054 for a selected patient. Patient report 2058 includes a graph 2116 of the device measurements received from the patient, as well as a listing of responses 2042 received from the patient. Specific techniques for writing a report generator program to display data in this manner are well known in the art.

Figure 211A:
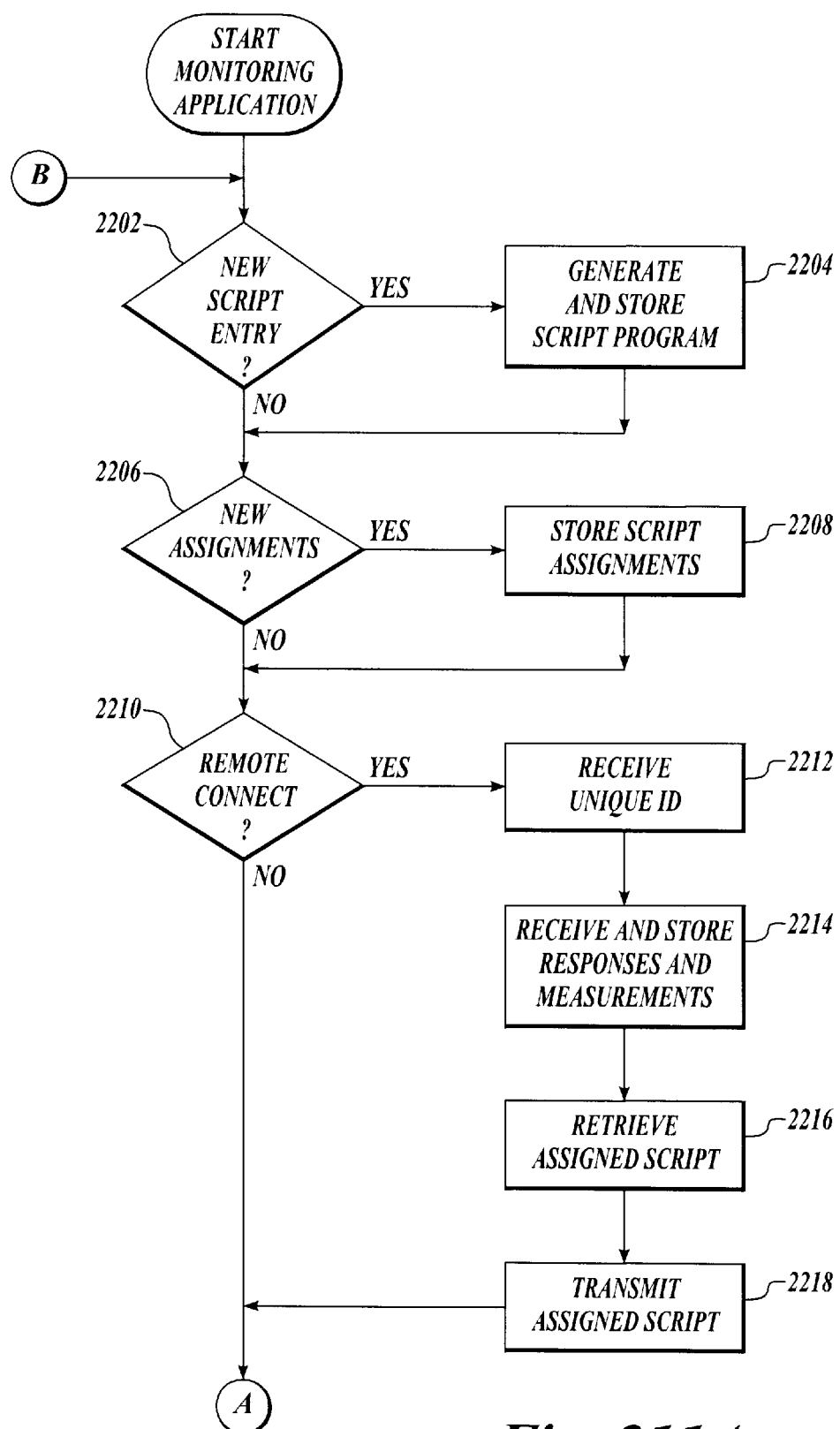
FIG. 211A is a flow chart illustrating the steps included in a monitoring application executed by the server of FIG. 201 according to the preferred embodiment of the invention.
Figure 211B:
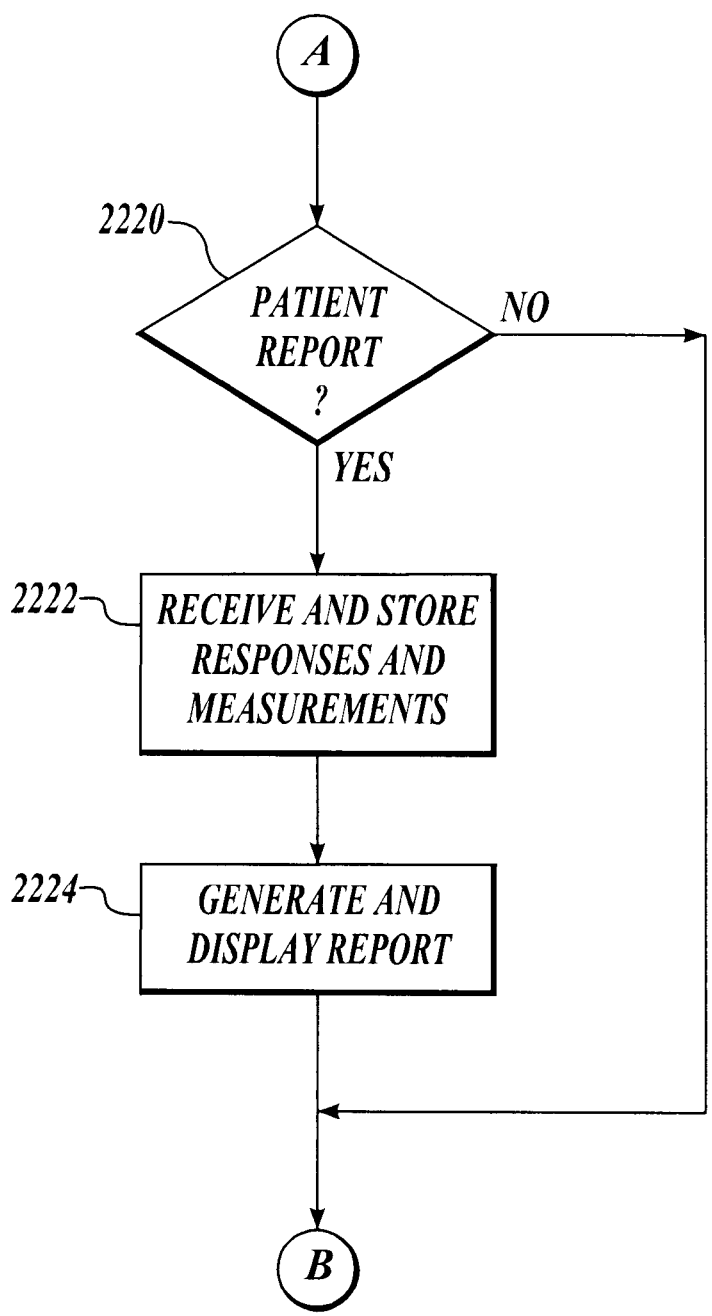
FIG. 211B is a continuation of the flow chart of FIG. 211A.

The operation of the preferred embodiment is illustrated in FIGS. 211–212. FIG. 211A is a flow chart illustrating steps included in the monitoring application executed by server 2018. FIG. 211B is a continuation of the flow chart of FIG. 211A. In step 2202, server 2018 determines if new script information has been entered through script entry screen 2056. If new script information has not been entered, server 2018 proceeds to step 2206. If new script information has been entered, server 2018 proceeds to step 2204.

As shown in FIG. 205, the script information includes a set of queries, and for each of the queries, corresponding responses choices. The script information also includes a selected monitoring device type from which to collect device measurements. The script information further includes a prescribed connection time for each apparatus to establish a subsequent communication link to the server. The script information is generally entered in server 2018 by a healthcare provider, such as the patients' physician or case manager. Of course, any person desiring to communicate with the patients may also be granted access to server 2018 to create and assign script programs. Further, it is to be understood that the system may include any number of remote interfaces for entering script generation and script assignment information in server 2018.

In step 2204, script generator 2050 generates a script program from the information entered in screen 2056. The script program is stored in database 2038. Steps 2202 and 2204 are preferably repeated to generate multiple script programs, e.g. a script program for diabetes patients, a script program for asthma patients, etc. Each script program corresponds to a respective one of the sets of queries entered through script entry screen 2056. Following step 2204, server 2018 proceeds to step 2206.

In step 2206, server 2018 determines if new script assignment information has been entered through assignment screen 2057. If new script assignment information has not been entered, server 2018 proceeds to step 2210. If new script assignment information has been entered, server 2018 proceeds to step 2208. As shown in FIG. 207, the script programs are assigned to each patient by selecting a script program through check boxes 2106, selecting the patients to whom the selected script program is to be assigned through check boxes 2108, and pressing the ASSIGN SCRIPT button 2112. When button 2112 is pressed, script assignor 2052 creates for each patient selected in check boxes 2108 a respective pointer to the script program selected in check boxes 2106. In step 2208, each pointer is stored in look-up table 2046 of database 2038. Following step 2208, server 2018 proceeds to step 2210.

In step 2210, server 2018 determines if any of the apparatuses are remotely connected to the server. Each patient to be monitored is preferably provided with his or her own apparatus which has the patient's unique identification code stored therein. Each patient is thus uniquely associated with a respective one of the apparatuses. If none of the apparatuses is connected, server 2018 proceeds to step 2220.

If an apparatus is connected, server 2018 receives from the apparatus the patient's unique identification code in step 2212. In step 2214, server 2018 receives from the apparatus the query responses 2042, device measurements 2044, and script identification code recorded during execution of a previously assigned script program. The script identification code identifies to the server which script program was executed by the apparatus to record the query responses and device measurements. The responses, device measurements, and script identification code are stored in database 2038.

In step 2216, server 2018 uses the patient identification code to retrieve from table 2046 the pointer to the script program assigned to the patient. The server then retrieves the assigned script program from database 2038. In step 2218, server 2018 transmits the assigned script program to the patient's apparatus through communication network 2024. Following step 2218, server 2018 proceeds to step 2220.

In step 2220, server 2018 determines if a patient report request has been received from workstation 2020. If no report request has been received, server 2018 returns to step 2202. If a report request has been received for a selected patient, server 2018 retrieves from database 2038 the measurements and query responses last received from the patient, step 2222. In step 2224, server 2018 generates and displays patient report 2058 on workstation 2020. As shown in FIG. 210, report 2058 includes the device measurements and query responses last received from the patient. Following step 2224, the server returns to step 2202.

Figure 212A:
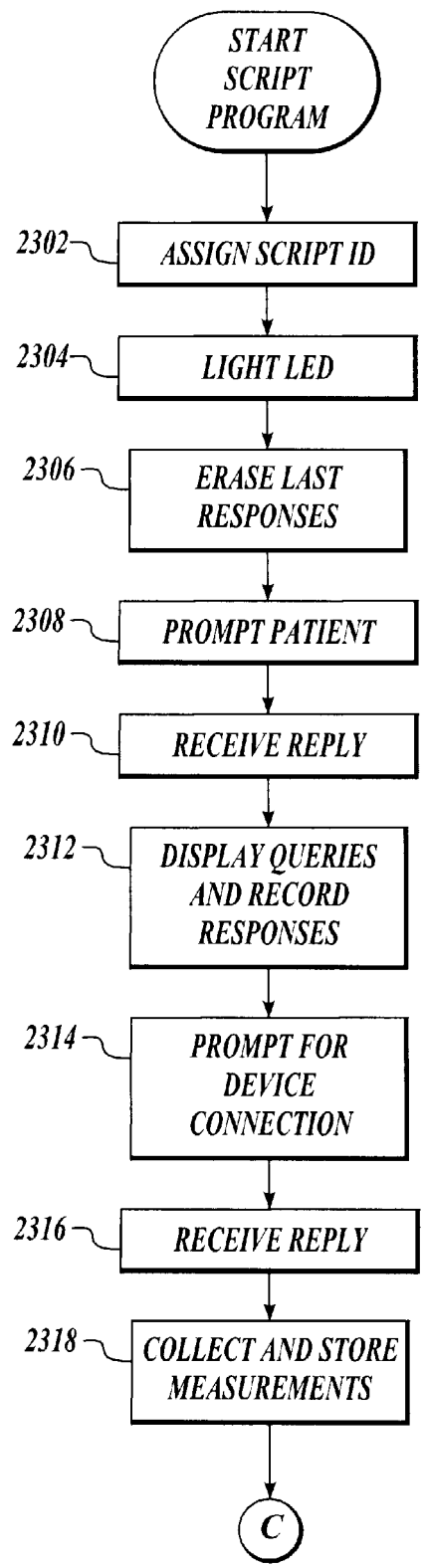
FIG. 212A is a flow chart illustrating the steps included in the script program of FIGS. 206A–206B.
Figure 212B:
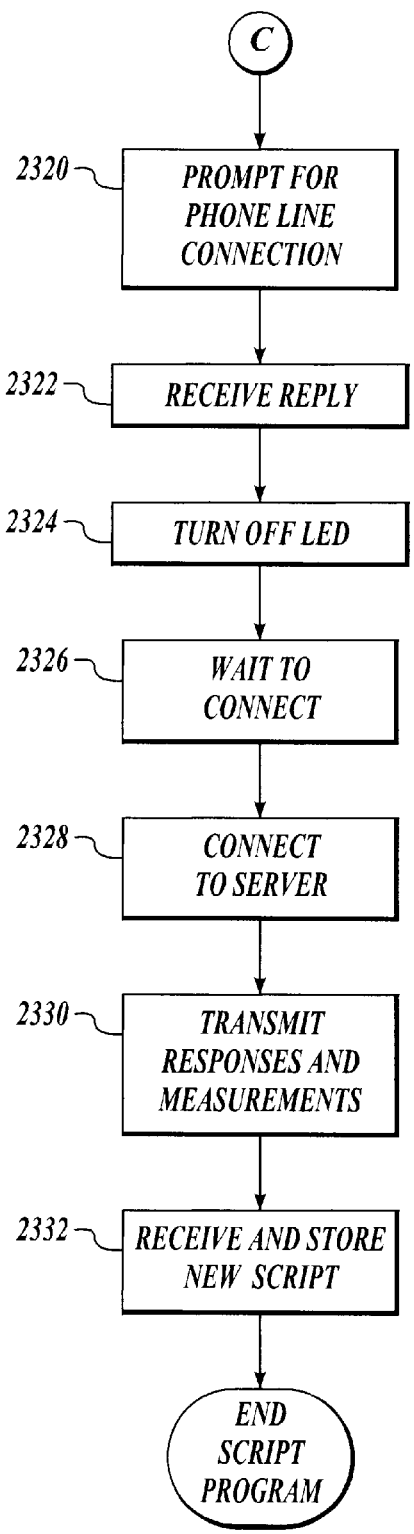
FIG. 212B is a continuation of the flow chart of FIG. 212A.

FIGS. 212A–212B illustrate the steps included in the script program executed by apparatus 2026. Before the script program is received, apparatus 2026 is initially programmed with the patient's unique identification code and the script interpreter used by microprocessor 2076 to execute the script program. The initial programming may be achieved during manufacture or during an initial connection to server 2018. Following initial programming, apparatus 2026 receives from server 2018 the script program assigned to the patient associated with apparatus 2026. The script program is received by modem 2086 through a first communication link and stored in memory 2080.

In step 2302, microprocessor 2076 assigns a script identification code to the script program and stores the script identification code in memory 2080. The script identification code is subsequently transmitted to the server along with the query responses and device measurements to identify to the server which script program was most recently executed by the apparatus. In step 2304, microprocessor 2076 lights LED 2074 to notify the patient that he or she has unanswered queries stored in apparatus 2026. LED 2074 preferably remains lit until the queries are answered by the patient. In step 2306, microprocessor 2076 erases from memory 2080 the last set of query responses recorded.

In step 2308, microprocessor 2076 prompts the patient by displaying on display 2064 "ANSWER QUERIES NOW? PRESS ANY BUTTON TO START". In step 2310, microprocessor 2076 waits until a reply to the prompt is received from the patient. When a reply is received, microprocessor 2076 proceeds to step 2312. In step 2312, microprocessor 2076 executes successive display and input commands to display the queries and response choices on display 2064 and to receive responses to the queries.

Figure 208:
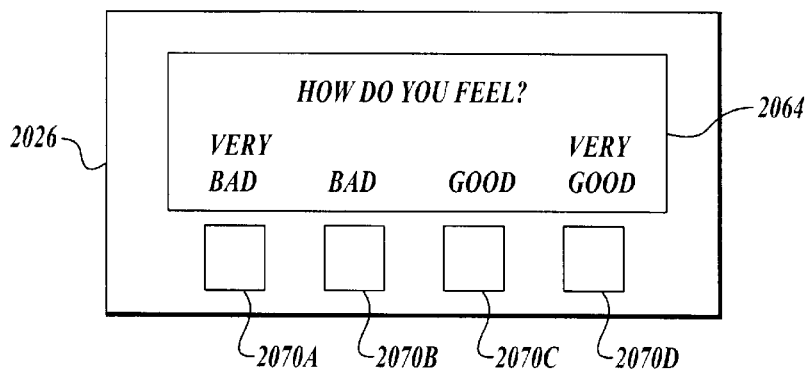
FIG. 208 is a sample query appearing on a display of the apparatus of FIG. 203.

FIG. 208 illustrates a sample query and its corresponding response choices as they appear on display 2064. The response choices are positioned on display 2064 such that each response choice is located proximate a respective one of the input buttons. In the preferred embodiment, each response choice is displayed immediately above a respective input button. The patient presses the button corresponding to his or her response. Microprocessor 2076 stores each response in memory 2080.

Figure 209:
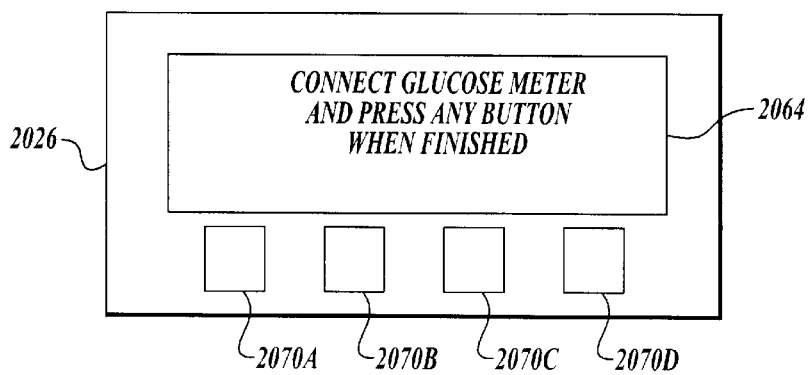
FIG. 209 is a sample prompt appearing on the display of the apparatus of FIG. 203.

In steps 2314–2318, microprocessor 2076 executes commands to collect device measurements from a selected monitoring device. The script program specifies the selected monitoring device from which to collect the measurements. In step 2314, microprocessor 2076 prompts the patient to connect the selected monitoring device, for example a blood glucose meter, to one of the device jacks. A sample prompt is shown in FIG. 209. In step 2316, microprocessor 2076 waits until a reply to the prompt is received from the patient. When a reply is received, microprocessor 2076 proceeds to step 2318. Microprocessor 2076 also connects UART 2078 to interface 2090 through switch 2088. In step 2318, microprocessor 2076 collects the device measurements from monitoring device 2028 through interface 2090. The measurements are stored in memory 2080.

In step 2320, microprocessor 2076 prompts the patient to connect apparatus 2026 to telephone jack 2022 so that apparatus 2026 may connect to server 2018 at the prescribed connection time. In step 2322, microprocessor 2076 waits until a reply to the prompt is received from the patient. When a reply is received, microprocessor 2076 turns off LED 2074 in step 2324. In step 2326, microprocessor 2076 waits until it is time to connect to server 2018. Microprocessor 2076 compares the connection time specified in the script program to the current time output by clock 2084. When it is time to connect, microprocessor 2076 connects UART 2078 to modem 2086 through switch 2088.

In step 2328, microprocessor 2076 establishes a subsequent communication link between apparatus 2026 and server 2018 through modem 2086 and communication network 2024. If the connection fails for any reason, microprocessor 2076 repeats step 2328 to get a successful connection. In step 2330, microprocessor 2076 transmits the device measurements, query responses, script identification code, and patient identification code stored in memory 2080 to server 2018 through the subsequent communication link. In step 2332, microprocessor 2076 receives through modem 2086 a new script program from server 2018. The new script program is stored in memory 2080 for subsequent execution by microprocessor 2076. Following step 2332, the script program ends.

One advantage of the monitoring system of the present invention is that it allows each patient to select a convenient time to respond to the queries, so that the monitoring system is not intrusive to the patient's schedule. A second advantage of the monitoring system is that it incurs very low communications charges because each remote apparatus connects to the server at times when communication rates are lowest. Moreover, the cost to manufacture each remote apparatus is very low compared to personal computers or Internet terminals, so that the monitoring system is highly affordable.

A third advantage of the monitoring system is that it allows each apparatus to be programmed remotely through script programs. Patient surveys, connection times, display prompts, selected monitoring devices, patient customization, and other operational details of each apparatus may be easily changed by transmitting a new script program to the apparatus. Moreover, each script program may be easily created and assigned by remotely accessing the server through the Internet. Thus, the invention provides a powerful, convenient, and inexpensive system for remotely monitoring a large number of patients.

Figure 213:
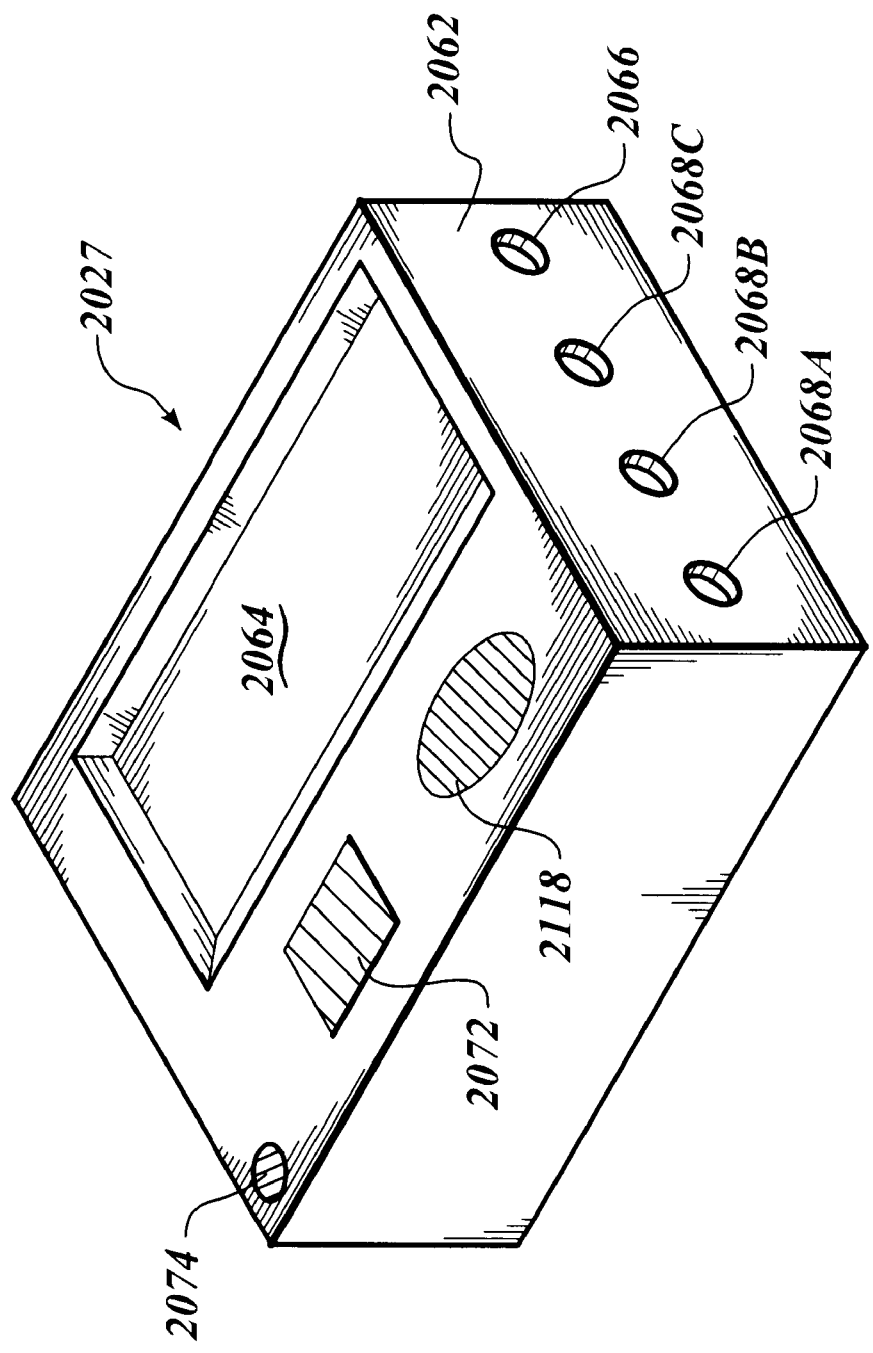
FIG. 213 is a perspective view of a remotely programmable apparatus according to a second embodiment of the invention.
Figure 214:
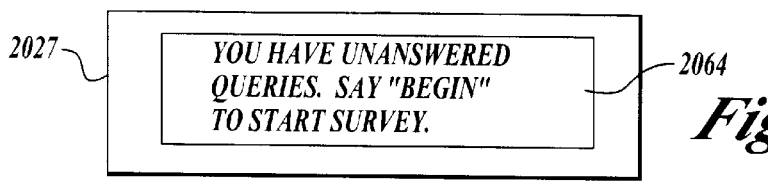
FIG. 214 is a sample prompt appearing on a display of the apparatus of FIG. 213.
Figure 215:
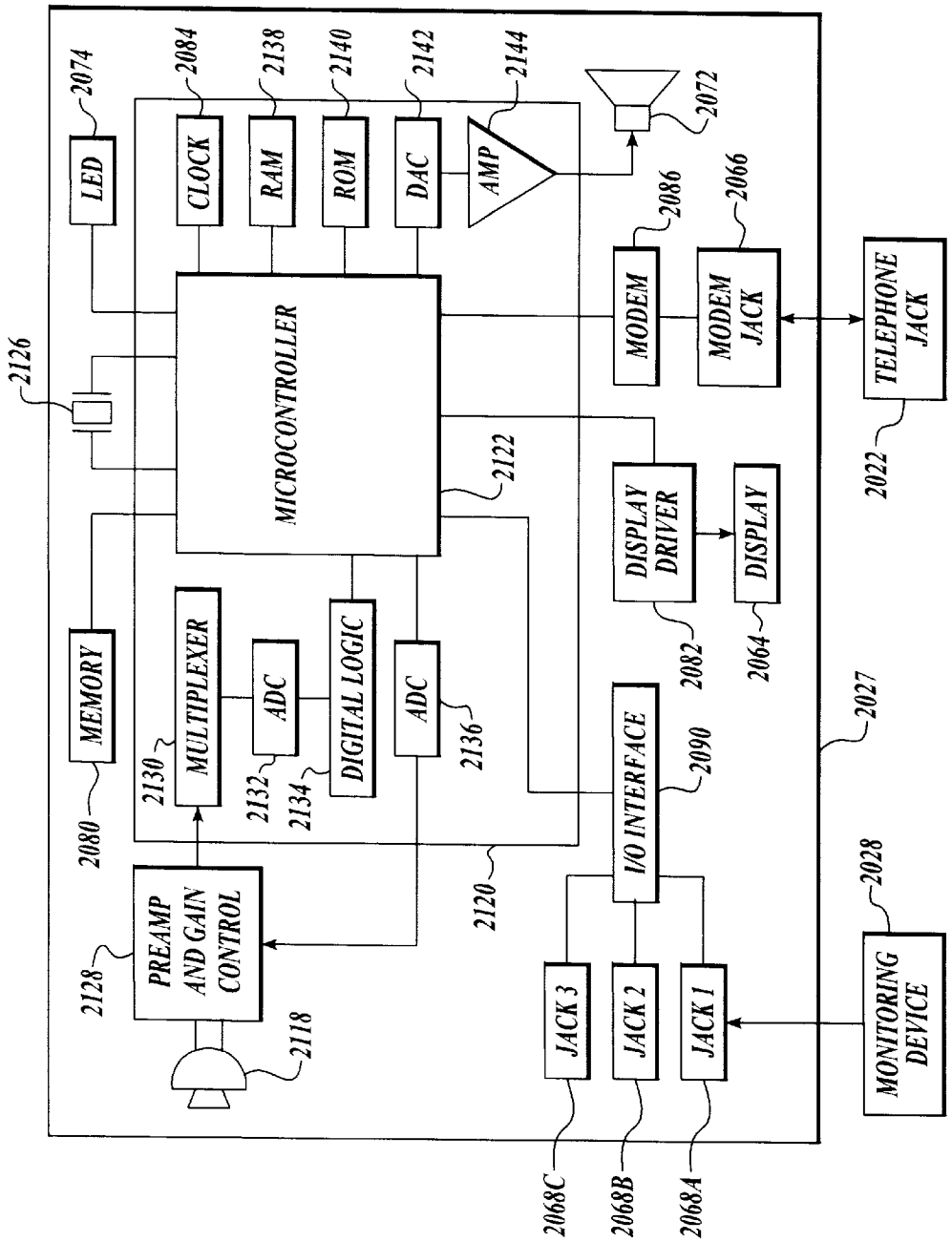
FIG. 215 is a block diagram illustrating the components of the apparatus of FIG. 213.

FIGS. 213–215 illustrate a second embodiment of the invention in which each remotely programmable apparatus has speech recognition and speech synthesis functionality. FIG. 213 shows a perspective view of an apparatus 2027 according to the second embodiment. Apparatus 2027 includes a speaker 2072 for audibly communicating queries and prompts to the patient. Apparatus 2027 also includes a microphone 2118 for receiving spoken responses to the queries and prompts. Apparatus 2027 may optionally include a display 2064 for displaying prompts to the patient, as shown in FIG. 214.

FIG. 215 is a schematic block diagram illustrating the components of apparatus 2027 in greater detail. Apparatus 2027 is similar in design to the apparatus of the preferred embodiment except that apparatus 2027 includes an audio processor chip 2120 in place of microprocessor 2076. Audio processor chip 2120 is preferably an RSC-164 chip commercially available from Sensory Circuits Inc. of 1735 N. First Street, San Jose, Calif. 95112.

Audio processor chip 2120 has a microcontroller 2122 for executing script programs received from the server. A memory 2080 is connected to microcontroller 2122. Memory 2080 stores the script programs and a script interpreter used by microcontroller 2122 to execute the script programs. Memory 2080 also stores measurements received from monitoring device 2028, responses to the queries, script identification codes, and the patient's unique identification code.

Audio processor chip 2120 also has built in speech synthesis functionality for synthesizing queries and prompts to a patient through speaker 2072. For speech synthesis, chip 2120 includes a digital to analog converter (DAC) 2142 and an amplifier 2144. DAC 2142 and amplifier 2144 drive speaker 2072 under the control of microcontroller 2122.

Audio processor chip 2120 further has built in speech recognition functionality for recognizing responses spoken into microphone 2118. Audio signals received through microphone 2118 are converted to electrical signals and sent to a preamp and gain control circuit 2128. Preamp and gain control circuit 2128 is controlled by an automatic gain control circuit 2136, which is in turn controlled by microcontroller 2122. After being amplified by preamp 2128, the electrical signals enter chip 2120 and pass through a multiplexer 2130 and an analog to digital converter (ADC) 2132. The resulting digital signals pass through a digital logic circuit 2134 and enter microcontroller 2122 for speech recognition.

Audio processor chip 2120 also includes a RAM 2138 for short term memory storage and a ROM 2140 which stores programs executed by microcontroller 2122 to perform speech recognition and speech synthesis. Chip 2120 operates at a clock speed determined by a crystal 2126. Chip 2120 also includes a clock 2084 which provides the current date and time to microcontroller 2122. As in the preferred embodiment, apparatus 2027 includes an LED 2074, display driver 2082, modem 2086, and device interface 2090, all of which are connected to microcontroller 2122.

The operation of the second embodiment is similar to the operation of the preferred embodiment except that queries, response choices, and prompts are audibly communicated to the patient through speaker 2072 rather than being displayed to the patient on display 2064. The operation of the second embodiments also differs from the operation of the preferred embodiment in that responses to the queries and prompts are received through microphone 2118 rather than through user input buttons.

The script programs of the second embodiment are similar to the script program shown in FIGS. 206A–206B, except that each display command is replaced by a speech synthesis command and each input command is replaced by a speech recognition command. The speech synthesis commands are executed by microcontroller 2122 to synthesize the queries, response choices, and prompts through speaker 2072. The speech recognition commands are executed by microcontroller 2122 to recognize responses spoken into microphone 2118.

For example, to ask the patient how he or she feels and record a response, microcontroller 2122 first executes a speech synthesis command to synthesize through speaker 2072 "How do you feel? Please answer with one of the following responses: very bad, bad, good, or very good." Next, microcontroller 2118 executes a speech recognition command to recognize the response spoken into microphone 2118. The recognized response is stored in memory 2080 and subsequently transmitted to the server. Other than the differences described, the operation and advantages of the second embodiment are the same as the operation and advantages of the preferred embodiment described above.

Although the first and second embodiments focus on querying individuals and collecting responses to the queries, the system of the invention is not limited to querying applications. The system may also be used simply to communicate messages to the individuals. FIGS. 216–219 illustrate a third embodiment in which the system is used to perform this automated messaging function. In the third embodiment, each script program contains a set of statements to be communicated to an individual rather than a set of queries to be answered by the individual. Of course, it will be apparent to one skilled in the art that the script programs may optionally include both queries and statements.

Figure 216:
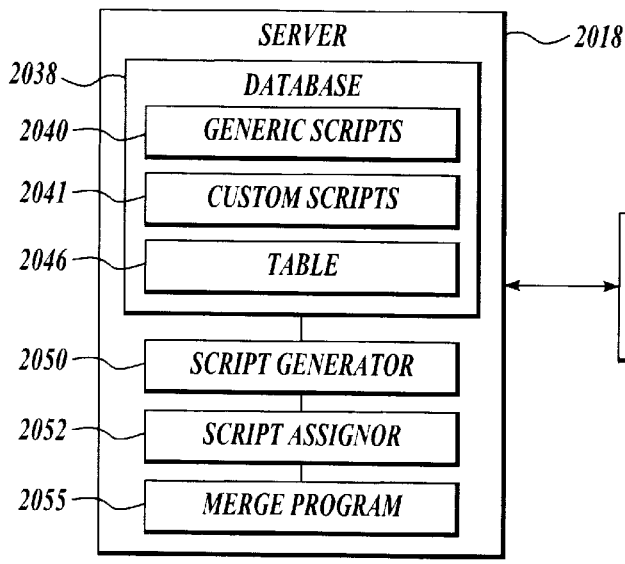
FIG. 216 is a schematic block diagram illustrating the interaction of the server of FIG. 201 with the apparatus of FIG. 203 according to a third embodiment of the invention.

The third embodiment also shows how the queries and statements may be customized to each individual by merging personal data with the script programs, much like a standard mail merge application. Referring to FIG. 216, personal data relating to each individual is preferably stored in look-up table 2046 of database 2038. By way of example, the data may include each individual's name, the name of each individual's physician, test results, appointment dates, or any other desired data. As in the preferred embodiment, database 2038 also stores generic script programs 2040 created by script generator 2050.

Figure 217:
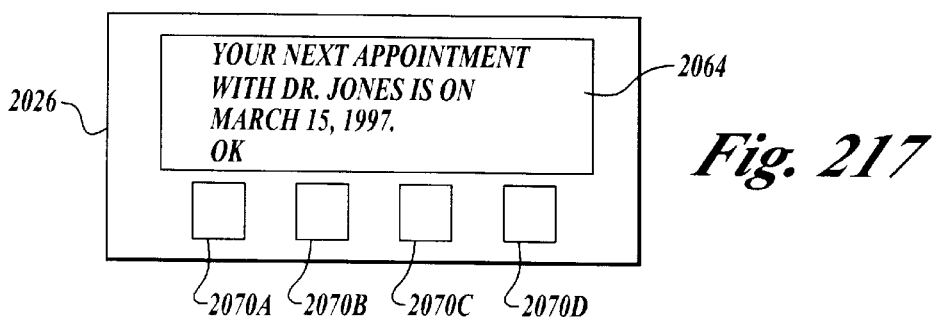
FIG. 217 is a first sample message appearing on the display of the apparatus of FIG. 203.
Figure 218:
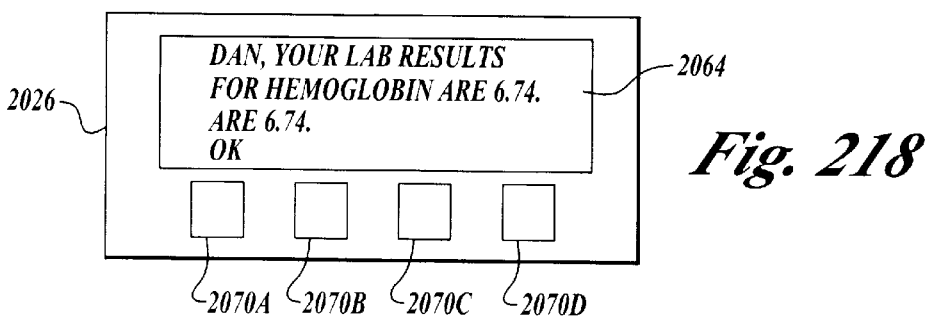
FIG. 218 is a second sample message appearing on the display of the apparatus of FIG. 203.

Server 2018 includes a data merge program 2055 for merging the data stored in table 2046 with generic script programs 2040. Data merge program 2055 is designed to retrieve selected data from table 2046 and to insert the data into statements in generic script programs 2040, thus creating custom script programs 2041. Each custom script program 2041 contains statements which are customized to an individual. For example, the statements may be customized with the individual's name, test results, etc. Examples of such customized statements are shown in FIGS. 217–218.

Figure 219:
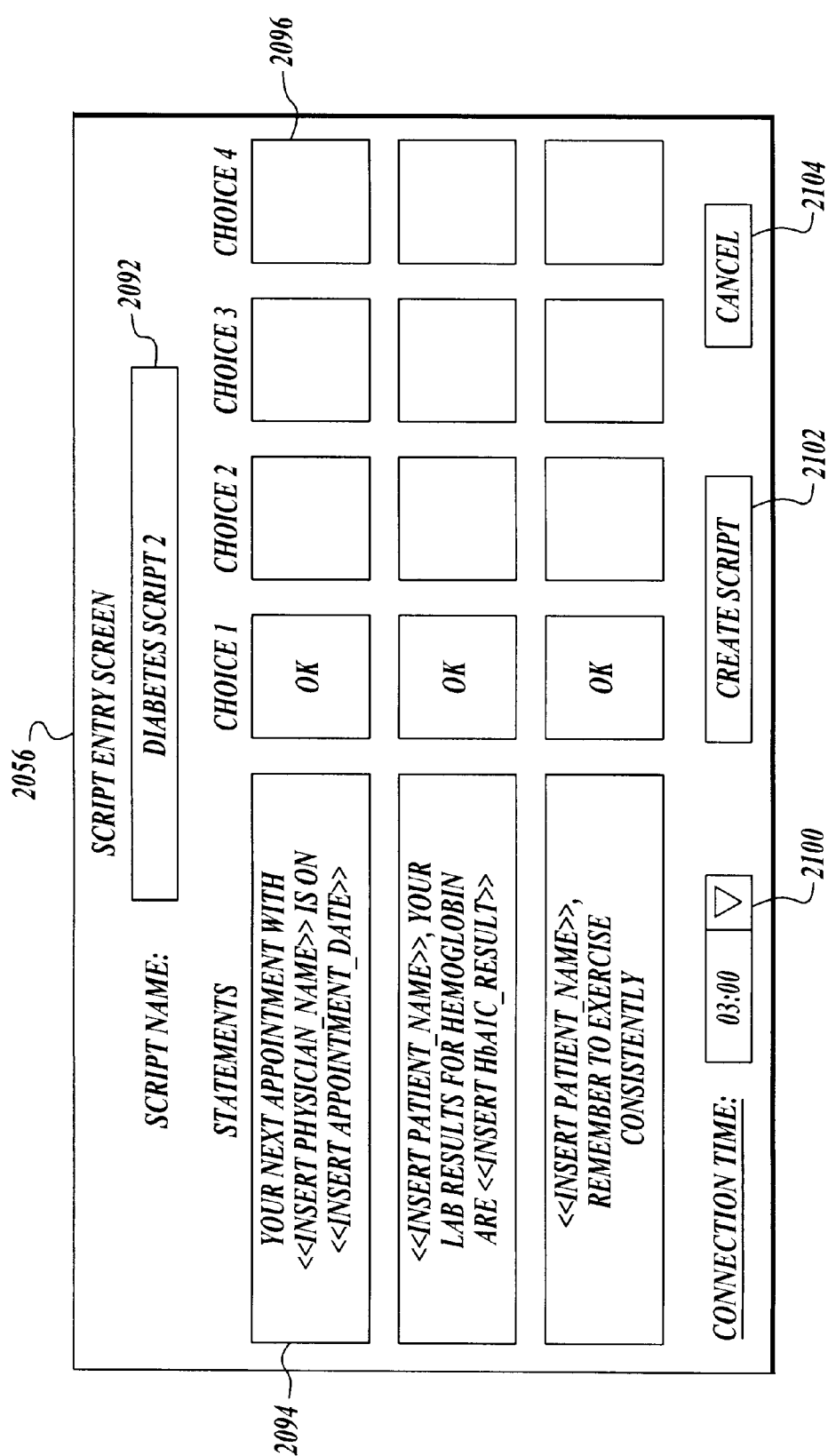
FIG. 219 is a script entry screen according to the third embodiment of the invention.

The operation of the third embodiment is similar to the operation of the preferred embodiment except that the script programs are used to communicate messages to the individuals rather than to query the individuals. Each message is preferably a set of statements. Referring to FIG. 219, the statements may be entered in the server through script entry screen 2056, just like the queries of the preferred embodiment.

Each statement preferably includes one or more insert commands specifying data from table 2046 to be inserted into the statement. The insert commands instruct data merge program 2055 to retrieve the specified data from database 2038 and to insert the data into the statement. For example, the insert commands shown in FIG. 219 instruct the data merge program to insert a physician name, an appointment date, a patient name, and a test result into the statements. As in the preferred embodiment, each statement may also include one or more response choices which are entered in fields 2096.

Following entry of the statements and response choices, CREATE SCRIPT button 2102 is pressed. When button 2102 is pressed, script generator 2050 generates a generic script program from the information entered in screen 2056. The generic script program is similar to the script program shown in FIGS. 206A–206B, except that the display commands specify statements to be displayed rather than queries. Further, the statements include insert commands specifying data to be inserted into the script program. As in the preferred embodiment, multiple script programs are preferably generated, e.g. a generic script program for diabetes patients, a generic script program for asthma patients, etc. The generic script programs are stored in database 2038.

Following generation of the generic script programs, server 2018 receives script assignment information entered through script assignment screen 2057. As shown in FIG. 207, the script programs are assigned by first selecting one of the generic script programs through check boxes 2106, selecting individuals through check boxes 2108, and pressing the ASSIGN SCRIPT button 2112. When button 2112 is pressed, data merge program 2055 creates a custom script program for each individual selected in check boxes 2108.

Each custom script program is preferably created by using the selected generic script program as a template. For each individual selected, data merge program 2055 retrieves from database 2038 the data specified in the insert commands. Next, data merge program 2055 inserts the data into the appropriate statements in the generic script program to create a custom script program for the individual. Each custom script program is stored in database 2038.

As each custom script program is generated for an individual, script assignor 2052 assigns the script program to the individual. This is preferably accomplished by creating a pointer to the custom script program and storing the pointer with the individual's unique identification code in table 2046. When the individual's remote apparatus connects to server 2018, server 2018 receives from the apparatus the individual's unique identification code. Server 2018 uses the unique identification code to retrieve from table 2046 the pointer to the custom script program assigned to the individual. Next, server 2018 retrieves the assigned script program from database 2038 and transmits the script program to the individual's apparatus through communication network 2024.

The apparatus receives and executes the script program. The execution of the script program is similar to the execution described in the preferred embodiment, except that statements are displayed to the individual rather than queries. FIGS. 217–218 illustrate two sample statements as they appear on display 2064. Each statement includes a response choice, preferably an acknowledgment such as "OK". After reading a statement, the individual presses the button corresponding to the response choice to proceed to the next statement. Alternatively, the script program may specify a period of time that each statement is to be displayed before proceeding to the next statement. The remaining operation of the third embodiment is analogous to the operation of the preferred embodiment described above.

Although it is presently preferred to generate a custom script program for each individual as soon as script assignment information is received for the individual, it is also possible to wait until the individual's apparatus connects to the server before generating the custom script program. This is accomplished by creating and storing a pointer to the generic script program assigned to the individual, as previously described in the preferred embodiment. When the individual's apparatus connects to the server, data merge program 2055 creates a custom script program for the individual from the generic script program assigned to the individual. The custom script program is then sent to the individual's apparatus for execution.

SUMMARY, RAMIFICATIONS, AND SCOPE

Although the above description contains many specificities, these should not be construed as limitations on the scope of the invention but merely as illustrations of some of the presently preferred embodiments. Many other embodiments of the invention are possible. For example, the scripting language and script commands shown are representative of the preferred embodiment. It will be apparent to one skilled in the art many other scripting languages and specific script commands may be used to implement the invention.

Moreover, the invention is not limited to the specific applications described. The system and method of the invention have many other applications both inside and outside the healthcare industry. For example, pharmaceutical manufacturers may apply the system in the clinical development and post marketing surveillance of new drugs, using the system as an interactive, on-line monitoring tool for collecting data on the efficacy, side effects, and quality of life impact of the drugs. Compared to the current use of labor intensive patient interviews, the system provides a fast, flexible, and cost effective alternative for monitoring the use and effects of the drugs.

The system may also be used by home healthcare companies to enhance the service levels provided to customers, e.g., panic systems, sleep surveillance, specific monitoring of disease conditions, etc. Alternatively, the system may be used to monitor and optimize the inventory of home stationed health supplies. As an example, the system may be connected to an appropriate measuring device to optimize timing of oxygen tank delivery to patients with COPD.

The system and method of the invention also have many applications outside the healthcare industry. For example, the system may be used for remote education over the Internet, facilitating educational communication with children or adult trainees who lack access to sophisticated and expensive computer equipment. The system may also be used by law enforcement officers to perform on-line surveillance of individuals on probation or parole.

Further, the invention has numerous applications for gathering data from remotely located devices. For example, the system may be used to collect data from smart appliances, such as identification check systems. Alternatively, the system may be applied to the remote monitoring of facilities, including safety and security monitoring, or to environmental monitoring, including pollution control and pipeline monitoring. Many other suitable applications of the invention will be apparent to one skilled in the art.

In terms of relating the new matter from application Ser. No. 08/946,341 (and its parent applications) to the original matter in this case, it will be readily appreciated and understood by one of ordinary skill in the art that many of the terms in the original case are the functional equivalent of, a particular embodiment of, and/or otherwise interchangeable with, terms in the detailed description which came from application Ser. No. 08/946,341. For example, in light of the foregoing description, and particularly comparing FIGS. 1 and 2 (from the original application) with FIGS. 201 and 202 (from application Ser. No. 08/946,341), it will be readily understood of ordinary skill that:

a) the remote clearinghouse 18 in FIG. 1 (and further identified as one part of an alternate embodiment of the remotely located digital signal processing unit 42 in FIG. 2), is equivalent to and interchangeable with server 2018 of FIG. 201, and vice versa;

b) in FIG. 1, the arrangement comprising data management unit 28 connected via cable 32 to microprocessor based unit 10 and to audiovisual display 14, is a particular embodiment of, and in that sense equivalent to and interchangeable with, the remote apparatus 1 (or remote apparatus 2) of FIGS. 201 and 202, and vice versa;

c) the arrangement comprising control switches 44 of FIG. 2 operated by the user in conjunction with or response to audiovisual display 14 (of FIG. 1 or 2) is an example, or particular embodiment, of a monitoring device 2028 of FIG. 201, and is in that sense equivalent to and interchangeable with monitoring device 2028, and, in certain embodiments, vice versa;

d) the audiovisual display 14 of FIG. 1 or 2 is equivalent to and interchangeable with the display 2064 of FIG. 203, and vice versa;

e) the four user input buttons 2070A, 2070B, 2070C, and 2070D, of FIG. 203 are examples of, or particular embodiments of, and are in that sense equivalent to and interchangeable with, the control switches 44 in FIG. 2, which are connected to microprocessor based unit 10 in FIG. 2;

f) the clinician's computer 22 in FIG. 1 is equivalent to and interchangeable with workstation 2020 of FIG. 201, and vice versa;

g) the communication network 2024 in FIG. 201 are examples of, and/or particular embodiments of, and are in that sense equivalent to and interchangeable with, the arrangement of communications links 20, 30 and 34 in FIG. 1, and 84 in FIG. 2, and vice versa;

h) the program instruction modules of the administrator program executed by the remotely located digital signal processing unit 42 in FIG. 2 are examples of, or particular embodiments of, and are in that sense equivalent to and interchangeable with, certain of the script programs 2040 executed by server 18 in FIG. 202, and vice versa.

The foregoing list merely identifies examples, and is not an exhaustive list.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A system for assessment of a psychological condition of a patient comprising:

(A) a patient system including:
(1) a display for displaying an image to the patient;
(2) a patient processor unit including a patient processor, a switch operable for supplying an electrical signal that is detectable by the patient processor, and circuit means responsive to signals supplied by the patient processor for generating the image on the display; and
(3) a memory for storing program instructions for displaying an image on the display for provoking operation of the switch, and for changing the image in response to the operation of the switch by the patient;

(B) a clinician system located remotely from the patient system and including:
(1) a memory for storing administrator program instructions for establishing a diagnostic assessment procedure and for retrieving a diagnostic signal which results from the operation of the switch and which is representative of a diagnostic measure indicated by the diagnostic assessment procedure, wherein the administrator program instructions further comprise a script and the diagnostic assessment procedure includes executing the script for displaying queries on the display and retrieving the patient's responses to the queries; and
(2) a clinician processor for executing at least one of the administrator program instructions; and (C) a communications link connectable in signal communication with the patient system and the clinician system for the exchange of signals between the patient system and the clinician system.

2. The system of claim 1 wherein the diagnostic assessment procedure established by the administrator program further comprises execution of the program instructions for administration of a diagnostic task selected from the group of tasks comprising:

a delayed reaction task with distractions;

a delayed reaction task without distractions;

a continuous performance task with distractions;

a continuous performance task without distractions.

3. The system of claim 1 wherein the administrator program further comprises program instructions for display of a main menu screen allowing a clinician using the clinician system to select a menu item from the group comprising:

opening of a new file for establishing the diagnostic assessment procedure for the patient;

opening an existing file for storing the diagnostic measure resulting from the diagnostic assessment procedure in the memory of the clinician's computer workstation;

opening an existing file for storing a particular configuration of the diagnostic assessment procedure in the memory of the clinician's computer workstation;

saving a file associated with a particular the patient;

closing a file;

producing the diagnostic assessment procedure;

storing the program instructions in the memory of the patient processor unit of the patient system; and initiating execution of the diagnostic assessment procedure with the patient processor unit that is connected to the clinician's computer workstation.

4. The system of claim 1 wherein the clinician system is a clinician computer workstation.

5. The system of claim 1 wherein the clinician processor of the clinician system further comprises an input/output unit connected in signal communication with the clinician processor and connectable in signal communication with peripheral devices selected from the group comprising:

a printer for printing diagnostic measurement information generated from the diagnostic measure resulting from the diagnostic assessment procedure;

a facsimile machine for displaying diagnostic measurement information generated from the diagnostic measure resulting from the diagnostic assessment procedure;

a receptacle for receiving a removable and insertable external memory unit; and a patient system located locally relative to the clinician processor and wherein the signal communication with the clinician processor is accomplished by a serial data cable.

6. The system of claim 5 wherein:

(A) the external memory unit connectable in signal communication with said input/output unit further comprises means for storage of the program instructions for controlling the operation of the patient processor unit and the diagnostic measurement information generated from the diagnostic measure resulting from the diagnostic assessment procedure; and (B) the patient processor unit includes a receptacle for receiving the external memory unit.

7. The system of claim 1 wherein the clinician system further comprises a clearinghouse:

(A) for receiving the diagnostic signal resulting from the interactive operation of the switch of at least one of the patient processor units; and (B) connectable in signal communication for data transmission with the clinician system.

8. The system of claim 7 wherein the administrator program instructions further comprise a script and the diagnostic assessment procedure includes executing the script for displaying queries on the display and retrieving the patient's responses to the queries.

9. The system of claim 8 wherein:

(A) the clearinghouse further comprises a server including a script generator capable of generating the script and a database means connected to the script generator for storing scripts created by the script generator; and (B) the clinician system further comprises means for entering into the server the queries to be responded to by the patient, and for causing the script generator to generate the script.

10. The system of claim 9 wherein the clearinghouse further comprises means for receiving and storing a plurality of the diagnostic signals from a plurality of the patient processor units.

11. The system of claim 10 wherein the program instructions for retrieving a diagnostic signal representative of a diagnostic measure resulting from the diagnostic assessment procedure further include program instructions for transmitting the plurality of diagnostic signals stored in the clearinghouse to the clinician system.

12. The system of claim 1 further comprising analytical signal processing means for executing at least one instruction from a set of instructions that performs one or more analyses of the patient's interactive operation of the switch in response to the image on the display for provoking operation of the switch.

13. The system of claim 12 wherein the analytical signal processing means is the patient processor unit, and wherein:

(A) the program instructions further include at least one instruction from the set of instructions which perform the one or more analyses;

(B) the patient processor unit is further programmable for executing the at least one instruction;

(C) the memory of the patient processor unit further comprises an addressable memory for storage of the diagnostic signal and the at least one instruction for implementing the analyses; and (D) the patient processor of the patient processor unit further comprises means for accessing the at least one instruction and processing the diagnostic signal stored in the addressable memory.

14. The system of claim 12 wherein the analytical signal processing means is the clinician processor of the remotely located clinician system, and wherein (A) the administrator program instructions further include at least one instruction from the set of instructions which perform the one or more analyses;

(B) the clinician processor is further programmable for executing the at least one instruction;

(C) the memory of the clinician processor further comprises an addressable memory for storage of the diagnostic signal retrieved as a result of execution of the administrator program instructions and the at least one instruction for implementing the analyses; and (D) the clinician processor further comprises means for accessing the at least one instruction and processing the diagnostic signal stored in the addressable memory.

15. The system of claim 12 wherein the analytical signal processing means is a clearinghouse; and wherein the clearinghouse:

(A) includes a memory for storing, and a processor for executing, program instructions for retrieving a diagnostic signal resulting from the operation of the switch and representative of a diagnostic measure indicated by the diagnostic assessment procedure; and is (B) connectable in signal communication for data transmission with the clinician system.

16. The system of claim 12 wherein the analytical signal processing means further comprises a data management unit, said data management unit being programmable for executing the at least one instruction from the set of instructions which perform the one or more analyses; and including:

(A) an addressable memory for storage of the diagnostic signal;

(B) means for accessing the at least one instruction and processing the diagnostic signal stored in the addressable memory; and (C) connecting means for connecting in signal communication with the patient processor unit for coupling and transmitting signals representative of the interactive operation of the switch from the patient processor unit to the data management unit.

17. A system for remotely assessing and monitoring the psychological condition of a patient, the system comprising:

(A) a server including:
  (1) a script generator for generating a script from clinician information;
  (2) a database coupled to the script generator for storing scripts created by the script generator;

(B) a clinician interface for:
  (1) receiving entered clinician information;
  (2) generating the script based upon the entered clinician information;

(C) a patient system comprising:
  (1) a remotely programmable apparatus including:
    a. a memory for storing the script;
    b. a processor that is coupled to the memory for implementing the script;
  (2) a user interface for displaying an output determined by the processor implementing the script;

(3) monitoring means for obtaining diagnostic signals representative of the psychiatric condition of the patient;
(4) circuitry for communicating signals between the remotely programmable apparatus, the user interface, and the monitoring means; and
(D) a communication link for providing communication between the patient system, the server and the clinician interface.

18. The system of claim 17 wherein the server comprises a web server for generating a web page for entry of the clinician information.

19. The system of claim 17 wherein the clinician information further comprises patient message information not intended to cause the script to elicit a response from the patient.

20. The system of claim 17 wherein the clinician information further comprises patient prompt information which is intended to cause the script to elicit a response from the patient.

21. The system of claim 20 wherein the patient prompt information is intended to cause the script to generate queries to be answered by the patient.

22. The system of claim 20 wherein the patient prompt information is intended to cause the script to generate instructions for the patient.

23. The system of claim 20 wherein:
(A) the remotely programmable apparatus provides the monitoring means for obtaining the diagnostic signals;
(B) the user interface is included within the remotely programmable apparatus;
(C) the memory for storing the script further includes memory for storing the diagnostic signals;
(D) the remotely programmable apparatus includes means for causing the diagnostic signals to be transmitted to the server via the communication link; and
(E) the clinician interface further comprises means for receiving the diagnostic signals from the server.

24. The system of claim 23 wherein:
(A) the remotely programmable apparatus further includes user input buttons operable for supplying an electrical signal that is detectable by the processor that is coupled to the memory;
(B) the user interface includes a display for displaying an image and presenting audible signals to the patient;
(C) the memory further comprises means for storing program instructions for generating the patient prompt information;
(D) the patient prompt information further comprises an animated sequence of images displayed on the display for provoking interactive operation of the user input buttons by the patient;
(E) the program instructions further cause changes to the animated sequence and generate the diagnostic signals in response to the patient's interactive operation of the user input buttons; and
(F) the communication provided by the communication link includes transmission of diagnostic signals from the patient system to the server and from the server to the clinician interface, and transmission of script from the server to the patient system.

25. The system of claim 24 wherein the animated sequence presents a diagnostic task selected from the group of tasks comprising:
a delayed reaction task with distractions;
a delayed reaction task without distractions;
a continuous performance task with distractions;
a continuous performance task without distractions.

26. The system of claim 20 wherein the monitoring means is a separate monitoring device that is connectable in signal communication with the remotely programmable apparatus of the patient system.

27. The system of claim 26 wherein the monitoring device further comprises:
(A) a display for displaying an image and presenting audible signals to the patient;
(B) a patient processor unit including:
(1) a patient processor;
(2) a switch operable for supplying an electrical signal that is detectable by the patient processor;
(3) circuitry responsive to signals supplied by the patient processor for generating a visual display on the display;
(4) a memory for storing program instructions for:
a. generating an animated sequence of images on the display for provoking interactive operation of the switch, and
b. changing the animated sequence and generating the diagnostic signal in response to interactive operation of the switch by the patient.

28. The system of claim 27 wherein the server comprises a web server for generating a web page for entry of the clinician information, and wherein the clinician interface is connected to the web server.

29. The system of claim 27 further comprising analytical signal processing means for executing at least one instruction from a set of instructions that performs one or more analyses of the patient's interactive operation of the switch of the patient processor unit in response to the animated sequence generated by the program instructions.

30. The system of claim 20 wherein the patient user interface includes a speech synthesis means for audibly communicating the patient prompt information to the patient; and wherein the patient prompt information includes a sequence of audio signals communicated by the speech synthesis means for provoking interactive operation of the user input buttons.

31. The system of claim 20 wherein the patient user interface includes a speech recognition means for receiving spoken responses to the patient prompt information.

32. The system of claim 20 wherein the patient user interface comprises a display for displaying the patient prompt information and user input buttons for entering the patient's responses; and wherein the patient prompt information includes an animated sequence of images on the display for provoking interactive operation of the user input buttons.

33. The system of claim 32 wherein the animated sequence presents a diagnostic task selected from the group of tasks comprising:
a delayed reaction task with distractions;
a delayed reaction task without distractions;
a continuous performance task with distractions;
a continuous performance task without distractions.

34. The system of claim 17 wherein the communication link includes means for establishing a first communication link to the server to receive the script and means for establishing a subsequent communication link to the server to transmit the responses, and wherein the script specifies a connection time at which to establish the subsequent communication link.

35. The system of claim 17 wherein the remotely programmable apparatus further includes notification means connected to the processor for notifying the patient that output of at least one of the scripts has not been communicated to the patient.

36. The system of claim 35 wherein the notification means is a visual indicator displayed by the user interface for visually notifying the patient.

37. The system of claim 35 wherein the notification means is an audible prompt displayed by the user interface for audibly notifying the patient.

38. The system of claim 17 further comprising a plurality of remotely programmable apparatuses in communication with the server for remotely monitoring a plurality of patients, wherein the database means includes means for storing a plurality of scripts, the clinician interface includes means for entering script assignment information, the server includes script assignment means for assigning to each of the patients at least one of the scripts from the database means in accordance with the script assignment information, and the database further includes means for storing a list of the patients, and for each of the patients, a respective pointer to the script assigned to the patient.

39. The system of claim 17 wherein the user interface of the patient system further comprises user input buttons and presents a diagnostic task selected from the group of tasks comprising:
  a delayed reaction task with distractions;
  a delayed reaction task without distractions;
  a continuous performance task with distractions;
  a continuous performance task without distractions.

40. The system of claim 17 wherein the monitoring means further comprises at least one monitoring device to gather the diagnostic signals representative of the psychological condition of the patient and to transmit the diagnostic signal to the remotely programmable apparatus, wherein the remotely programmable apparatus further includes a device interface means connected to the processor for receiving the diagnostic signals from the monitoring device, and wherein the memory for storing the script includes memory for storing the diagnostic signals, and the communication provided by the communication link includes transmission of the diagnostic signals to the server.

41. The system of claim 40 wherein the device interface means includes means for interfacing with a plurality of monitoring devices, and the script specifies a selected monitoring device from which to collect the diagnostic signals.

42. The system of claim 40 wherein the server further comprises report means for reporting the responses and the diagnostic signals to the clinician interface.

43. The system of claim 40 wherein the monitoring device further comprises:
  (A) a display for displaying an image and presenting audible signals to the patient;
  (B) a patient processor unit connectable in signal communication with the remotely programmable apparatus and including:
    (1) a patient processor;
    (2) a switch operable for supplying an electrical signal that is detectable by the patient processor;
    (3) circuit means responsive to signals supplied by the patient processor for generating a visual display on the display;
    (4) a memory for storing program instructions for:
      a. generating an animated sequence of images on the display for provoking interactive operation of the switch, and
      b. changing the animated sequence and generating the diagnostic signals in response to interactive operation of the switch by the patient;
  (C) means for transmitting the diagnostic signals from the patient processor unit to the remotely programmable apparatus.

44. A method of assessing and monitoring the psychological condition of a patient comprising the method steps of:
  (A) receiving a script at a patient apparatus;
  (B) executing the script to generate a series of stimuli on a display;
  (C) including within the series a stimulus for provoking interactive operation of a switch by the patient;
  (D) executing an analytical signal processing instruction that analyses the patient's interactive operation of the switch in response to the series of stimuli;
  (E) generating a diagnostic measure from the analysis of the interactive operation of the switch; and
  (F) transmitting a diagnostic signal representative of the diagnostic measure to a clinician system located remotely from the patient by means of a communication link.

45. The method of claim 44 further comprising the method steps of:
  (A) executing an administrator program instruction for prescribing a diagnostic assessment procedure for obtaining the diagnostic measure;
  (B) retrieving the diagnostic signal representative of the diagnostic measure prescribed by the diagnostic assessment procedure via the communication link;
  (C) storing the diagnostic signal in a memory coupled to the communication link.

46. The method of claim 44 wherein the display further includes a visual display, wherein the stimuli includes visual stimuli, and wherein the stimulus for provoking interactive operation of the switch is a visual stimulus.

47. The method of claim 44 wherein the display includes an audio display, wherein the stimuli includes auditory stimuli, and wherein the stimulus for provoking interactive operation of the switch is an auditory stimulus.

48. A method for remotely assessing and monitoring the psychological condition of a patient, the method comprising the following steps:
  entering clinician information;
  generating a script based on the clinician information
  transmitting the script to a server, and from the server to a patient apparatus through a communication link;
  executing the script at the patient apparatus for generating output for the patient, wherein the output generated by execution of the scripts comprises output of a type selected from the group comprising:
    (A) messages for the patient's information which are not intended to elicit a patient reply to be transmitted to the server;
    (B) queries intended to elicit a patient reply to be transmitted to the server;
    (C) prescriptive instructions intended to cause the patient to perform a patient-administered diagnostic procedure and to communicate the results of the procedure to the server through the patient apparatus and the communication link.

49. The method of claim 48:
  (A) wherein the step of entering the clinician information comprises a step selected from the group of steps comprising:

(1) entering script information for generation of the script through a script entry means;
(2) assigning a predefined script to a specific patient through a script assignment means;
(3) modifying a predefined script through the script entry means;
(4) creating a new script through the script entry means; and (B) further comprising the step of providing means within the server for storing information selected from the following types of information:
(1) the script;
(2) the patient replies to the queries; and
(3) the results of the patient-administered diagnostic procedure.

50. The method of claim 49 wherein the server comprises a web server; wherein the script entry means and script assignment means further comprise a web page hosted on the web server, wherein the clinician information is entered by accessing the web page through the Internet and wherein the step of entering clinician information comprises the step of entering the clinician information in the web page.

51. The method of claim 49 further comprising the steps of:
providing a plurality of patients with a corresponding plurality of patient apparatuses such that each of the patients is associated with a respective one of the patient apparatuses,
entering in the server a plurality of sets of the clinician information;
generating in the server a plurality of scripts such that each of the scripts corresponds to a respective one of the sets of clinician information;
assigning to each of the patients at least one of the scripts;
storing in the server the scripts, a list of the patients, and for each of the patients, a respective pointer to the script assigned to the patient; and
transmitting to each of the patient apparatuses the script assigned to the patient associated with the patient apparatus.

52. The method of claim 48 wherein the patient apparatus includes a device interface for receiving the results from the patient-administered diagnostic procedure, and wherein the method further comprises the steps of: collecting the results in the patient apparatus through the device interface; transmitting the results from the patient apparatus to the server; and receiving and storing the results in the server.

53. The method of claim 52 wherein the device interface includes means for interfacing with a plurality of monitoring devices, the script specifies a selected monitoring device from which to collect the diagnostic signals, and the method further comprises the step of prompting the patient to connect the selected monitoring device to the device interface.

54. The method of claim 52 wherein the patient-administered diagnostic procedure comprises the method step of operating a monitoring device to generate the results, wherein the results further comprise diagnostic signals representative of diagnostic measurements of a psychological condition of a patient.

55. The method of claim 54 further comprising the step of reporting on a remote interface the diagnostic signals received in the server.

56. The method of claim 54 further comprising the method steps of:
(A) providing as the monitoring device a patient processor unit;
(B) providing for the patient processor unit:
(1) a patient processor,
(2) a switch operable for supplying an electrical signal that is detectable by the patient processor,
(3) circuit means responsive to signals supplied by the patient processor for generating a visual display on the display,
(4) a memory for storing program instructions;
(C) operating the monitoring device by executing the program instructions for performing the method steps of:
(1) generating an animated sequence of images on the display for provoking interactive operation of the switch, and
(2) causing operation of the patient processor and changing the animated sequence in response to interactive operation of the switch by the patient.

57. The method of claim 56 wherein the animated sequence of images presents a psychiatric diagnosis task selected from the group comprising:
a delayed reaction task with distractions;
a delayed reaction task without distractions;
a continuous performance task with distractions; and
a continuous performance task without distractions.

58. The method of claim 48 wherein the script is transmitted from the server to the patient apparatus through a first communication link, the responses to the script output presented to the patient are transmitted from the patient apparatus to the server through a subsequent communication link, the script specifies a connection time at which to establish the subsequent communication link.

59. The method of claim 48 wherein the patient apparatus includes a user interface; the user interface including a display and input buttons, and wherein the script output presented to the patient is communicated through the display and the patient responses to the output are received through the input buttons.

60. The method of claim 48 wherein the patient apparatus includes a user interface; the user interface including a speech synthesizer, and wherein the script output presented to the patient is communicated through the speech synthesizer.

61. The method of claim 48 wherein the patient apparatus includes a user interface; and wherein the user interface includes a speech recognizer for receiving the patient replies and the results of the procedure.

62. The method of claim 48 further comprising the steps of:
providing a plurality of patients with a plurality of patient apparatuses such that each of the patients is associated with a respective one of the patient apparatuses;
entering in the server a plurality of sets of the clinician information, generating in the server a plurality of scripts such that each of the scripts corresponds to a respective one of the sets of clinician information;
assigning to each of the patients at least one of the scripts;
storing in the server the scripts, a list of the patients, and for each of the patients, a respective pointer to the script assigned to the patient; and
transmitting to each of the patient apparatuses the script assigned to the patient associated with the patient apparatus.

63. The method of claim 62 wherein the patient apparatus includes a device interface for receiving the results from the patient-administered diagnostic procedure, and wherein the method further comprises the steps of: collecting the results in the patient apparatus through the device interface; transmitting the results from the patient apparatus to the server; and receiving and storing the results in the server.

64. The method of claim 63 wherein the patient-administered diagnostic procedure comprises the method step of operating a monitoring device to generate the results, wherein the results further comprise diagnostic signals representative of diagnostic measurements of a psychological condition of a patient.

65. The method of claim 64 wherein:
(A) the monitoring device further comprises a patient processor unit including:
   (1) a patient processor,
   (2) a switch operable for supplying an electrical signal that is detectable by the patient processor,
   (3) circuitry responsive to signals supplied by the patient processor for generating a visual display on the display,
   (4) a memory for storing program instructions; and (B) the step of operating the monitoring device further comprises the method step of executing the program instructions for performing the method steps of:
   (1) generating an animated sequence of images on the display for provoking interactive operation of the switch; and
   (2) causing operation of the patient processor and changing the animated sequence in response to interactive operation of the switch by the patient.

66. The method of claim 65 wherein the animated sequence of images presents a psychiatric diagnosis task selected from the group comprising:

a delayed reaction task with distractions;

a delayed reaction task without distractions;

a continuous performance task with distractions;

a continuous performance task without distractions.

* * * * *